US011503991B2

(12) United States Patent
Zeien

(10) Patent No.: US 11,503,991 B2
(45) Date of Patent: *Nov. 22, 2022

(54) FULL-FIELD THREE-DIMENSIONAL SURFACE MEASUREMENT

(71) Applicant: Virtual 3-D Technologies Corp., Charlton, MA (US)

(72) Inventor: Robert Zeien, Charlton, MA (US)

(73) Assignee: Virtual 3-D Technologies Corp., Cutchogue, NY (US)

(*) Notice: Subject to any disclaimer, the term of this patent is extended or adjusted under 35 U.S.C. 154(b) by 177 days.

This patent is subject to a terminal disclaimer.

(21) Appl. No.: 16/803,299

(22) Filed: Feb. 27, 2020

(65) Prior Publication Data

US 2020/0187764 A1 Jun. 18, 2020

Related U.S. Application Data

(63) Continuation-in-part of application No. 15/894,567, filed on Feb. 12, 2018, now Pat. No. 11,153,696, and (Continued)

(51) Int. Cl.
*A61B 5/00* (2006.01)
*G06T 7/521* (2017.01)
(Continued)

(52) U.S. Cl.
CPC .............. *A61B 1/051* (2013.01); *A61B 1/005* (2013.01); *A61B 1/00016* (2013.01); (Continued)

(58) Field of Classification Search
CPC ....... G01B 11/25; G01B 11/2522; G06T 7/50; G06T 7/521
See application file for complete search history.

(56) References Cited

U.S. PATENT DOCUMENTS

| 4,641,972 A | 2/1987 | Halioua et al. |
| 5,016,173 A | 5/1991 | Kenet et al. |

(Continued)

FOREIGN PATENT DOCUMENTS

| CN | 101264002 A | 9/2008 |
| CN | 101716077 A | 6/2010 |

(Continued)

OTHER PUBLICATIONS

Gastrointestinal system (www.rn.com/clinical-insights/gastrointestinal-system/, 2018).*

(Continued)

*Primary Examiner* — Carolyn A Pehlke
(74) *Attorney, Agent, or Firm* — Potomac Law Group, PLLC

(57) ABSTRACT

Embodiments of the present invention may be used to perform measurement of surfaces, such as external and internal surfaces of the human body, in full-field and in 3-D. Embodiments of the present invention may include an electromagnetic radiation source, which may be configured to project electromagnetic radiation onto a surface. The electromagnetic radiation source may be configured to project the electromagnetic radiation in a pattern corresponding to a spatial signal modulation algorithm. The electromagnetic radiation source may also be configured to project the electromagnetic radiation at a frequency suitable for transmission through the media in which the radiation is projected. An image sensor may be configured to capture image data representing the projected pattern. An image-processing module may be configured to receive the captured image data from the image sensor and to calculate a full-field, 3-D representation of the surface using the captured image data and the spatial signal modulation algorithm. A display (Continued)

device may be configured to display the full-field, 3-D representation of the surface.

18 Claims, 7 Drawing Sheets

Related U.S. Application Data a continuation-in-part of application No. 15/252,685, filed on Aug. 31, 2016, now Pat. No. 10,575,719, which is a continuation of application No. 13/830,477, filed on Mar. 14, 2013, now Pat. No. 9,456,752.

(60) Provisional application No. 62/458,691, filed on Feb. 14, 2017.

(51) Int. Cl.
*G01B 11/25* (2006.01)
*A61B 1/05* (2006.01)
*A61B 1/00* (2006.01)
*A61B 1/005* (2006.01)
*A61B 1/04* (2006.01)
*A61B 1/07* (2006.01)
*A61B 1/015* (2006.01)
*A61B 1/018* (2006.01)

(52) U.S. Cl.
CPC .......... *A61B 1/00032* (2013.01); *A61B 1/015* (2013.01); *A61B 1/018* (2013.01); *A61B 1/041* (2013.01); *A61B 1/07* (2013.01); *A61B 5/0077* (2013.01); *A61B 5/0086* (2013.01); *G01B 11/25* (2013.01); *G01B 11/2522* (2013.01); *G06T 7/521* (2017.01); *A61B 5/0073* (2013.01); *A61B 5/0084* (2013.01); *G06T 2200/32* (2013.01)

(56) References Cited

U.S. PATENT DOCUMENTS

| | | | |
|---|---|---|---|
| 5,363,839 A | 11/1994 | Lankford |
| 5,487,012 A | 1/1996 | Topholm et al. |
| 5,581,352 A | 12/1996 | Zeien |
| 5,587,832 A | 12/1996 | Krause |
| 5,615,003 A | 3/1997 | Hermary et al. |
| 5,784,098 A | 7/1998 | Shoji et al. |
| 5,847,832 A | 12/1998 | Liskow et al. |
| 6,084,712 A | 7/2000 | Harding |
| 6,115,058 A | 9/2000 | Omori et al. |
| 6,134,003 A | 10/2000 | Tearney et al. |
| 6,178,346 B1 | 1/2001 | Amundson et al. |
| 6,332,087 B1 | 12/2001 | Svenson et al. |
| 6,364,831 B1 | 4/2002 | Crowley |
| 6,475,138 B1 | 11/2002 | Schechter et al. |
| 6,503,195 B1 | 1/2003 | Keller et al. |
| 6,579,285 B2 | 6/2003 | Sinofsky |
| 6,695,779 B2 | 2/2004 | Sauer et al. |
| 6,832,984 B2 | 12/2004 | Stelzer et al. |
| 7,153,299 B1 | 12/2006 | Tu et al. |
| 7,385,708 B2 | 6/2008 | Ackerman et al. |
| 7,492,398 B1 | 2/2009 | Norita et al. |
| 7,728,868 B2 | 6/2010 | Razzaque et al. |
| 7,734,061 B2 | 6/2010 | Breed et al. |
| 7,742,232 B2 | 6/2010 | Cho et al. |
| 7,747,067 B2 | 6/2010 | Popescu et al. |
| 7,751,694 B2 | 7/2010 | Cho et al. |
| 7,812,968 B2 | 10/2010 | Bendall et al. |
| 7,821,649 B2 | 10/2010 | Bendall et al. |
| 7,846,107 B2 | 12/2010 | Hoffman et al. |
| 8,094,322 B2 | 1/2012 | Mayer et al. |
| 8,105,233 B2 | 1/2012 | Kheir |
| 8,123,722 B2 | 2/2012 | Chang et al. |
| 8,235,985 B2 | 8/2012 | Saadat et al. |
| 8,419,613 B2 | 4/2013 | Saadat et al. |
| 8,422,030 B2 | 4/2013 | Bendall et al. |
| 8,900,219 B2 | 12/2014 | Sinofsky et al. |
| 9,254,103 B2 | 2/2016 | Krishnaswamy et al. |
| 9,326,668 B1 | 5/2016 | Berbee et al. |
| 9,456,752 B2 | 10/2016 | Zeien |
| 9,867,528 B1 | 1/2018 | Boppart et al. |
| 2003/0023141 A1 | 1/2003 | Stelzer et al. |
| 2003/0164952 A1 | 9/2003 | Deichmann et al. |
| 2003/0174208 A1 | 9/2003 | Glukhovsky et al. |
| 2004/0133085 A1 | 7/2004 | Hall |
| 2004/0254474 A1 | 12/2004 | Seibel et al. |
| 2005/0088435 A1 | 4/2005 | Geng |
| 2005/0168735 A1 | 8/2005 | Boppart et al. |
| 2005/0182295 A1 | 8/2005 | Soper et al. |
| 2005/0219552 A1 | 10/2005 | Ackerman et al. |
| 2006/0270929 A1 | 11/2006 | Bouma et al. |
| 2007/0238955 A1 | 10/2007 | Tearney et al. |
| 2009/0118622 A1 | 5/2009 | Durkin et al. |
| 2009/0137952 A1 | 5/2009 | Ramamurthy et al. |
| 2009/0208143 A1 | 8/2009 | Yoon et al. |
| 2009/0259102 A1 | 10/2009 | Koninckx et al. |
| 2009/0296980 A1 | 12/2009 | Yi |
| 2010/0141829 A1 | 6/2010 | Jalali et al. |
| 2010/0160904 A1 | 6/2010 | McMillan et al. |
| 2011/0026037 A1 | 2/2011 | Forster et al. |
| 2011/0057930 A1 | 3/2011 | Keller et al. |
| 2011/0205552 A1 | 8/2011 | Bendall et al. |
| 2011/0242285 A1 | 10/2011 | Byren |
| 2011/0273548 A1 | 11/2011 | Uchiyama et al. |
| 2012/0029829 A1 | 2/2012 | Li et al. |
| 2012/0035434 A1 | 2/2012 | Ferren et al. |
| 2012/0059224 A1 | 3/2012 | Wellen et al. |
| 2012/0177283 A1 | 7/2012 | Wang et al. |
| 2012/0212595 A1 | 8/2012 | Parmar et al. |
| 2013/0027515 A1* | 1/2013 | Vinther ................. A61B 1/227 348/E13.02 |
| 2013/0044185 A1 | 2/2013 | Krishnaswamy et al. |
| 2013/0237754 A1 | 9/2013 | Berglund et al. |
| 2014/0012141 A1 | 1/2014 | Kim et al. |
| 2014/0063204 A1 | 3/2014 | Siercks |
| 2014/0085421 A1 | 3/2014 | Kuth et al. |
| 2014/0171743 A1 | 6/2014 | Heine et al. |
| 2014/0240464 A1 | 8/2014 | Lee |
| 2014/0375784 A1 | 12/2014 | Massetti |
| 2015/0049331 A1 | 2/2015 | Ri |
| 2015/0097968 A1 | 4/2015 | Bergman et al. |
| 2015/0098636 A1 | 4/2015 | Bergman et al. |
| 2016/0374546 A1 | 12/2016 | Berbee et al. |
| 2017/0027448 A1 | 2/2017 | Carr et al. |
| 2017/0041576 A1 | 2/2017 | Kobayashi |
| 2017/0071509 A1 | 3/2017 | Pandey et al. |
| 2017/0195809 A1 | 7/2017 | Teran et al. |
| 2018/0000336 A1 | 1/2018 | Gilad-Gilor et al. |
| 2018/0125345 A1 | 5/2018 | Rebella et al. |
| 2018/0156599 A1 | 6/2018 | Boppart et al. |
| 2018/0168440 A1 | 6/2018 | Das et al. |
| 2019/0038135 A1 | 2/2019 | Lee et al. |
| 2020/0060550 A1* | 2/2020 | Pesach ................. G06K 9/3233 |

FOREIGN PATENT DOCUMENTS

| | | |
|---|---|---|
| CN | 102575928 A | 7/2012 |
| CN | 102725688 A | 10/2012 |
| CN | 202714941 U | 2/2013 |
| CN | 102575928 B | 5/2015 |
| JP | 2003529432 A | 10/2003 |
| JP | 2008173397 A | 7/2008 |
| JP | 2009273655 A | 11/2009 |
| JP | 2010179021 A | 8/2010 |
| WO | 2001076452 A2 | 10/2001 |
| WO | 2010143692 A1 | 12/2010 |
| WO | 2011027127 A2 | 3/2011 |
| WO | 2011120526 A1 | 10/2011 |
| WO | 2012059253 A1 | 5/2012 |
| WO | WO-2018113885 A1 * | 6/2018 ......... G02B 23/2423 |

(56) References Cited

OTHER PUBLICATIONS

AIA indicator decision table, 2013.*
Azim, S. (Lantos Technologies), "Making a Digital Impression Using 3D Ear Canal Scanning," hearingreview.com (2012).
Barrera, F., et al., "Optical and Spectroscopic Properties of Human Whole Blood and Plasma with and without Y2O3 and Nd3+:Y2O3 Nanoparticles," Lasers Med Sci, 8 pages (Feb. 2013).
Cardiac Procedures and Surgeries At-A-Glance, American Heart Association/American Stroke Association, 4 pages, 2012.
Eagle Eye Platinum RX Digital IVUS Catheter, Volcano Precision Guided Therapy, product brochure, printed 2012, 4 pages.
Evans, J.L., et al., Accurate Three-Dimensional Reconstruction of Intravascular Ultrasound Data, Circulation (American Heart Association, Inc.), 93, pp. 567-576 (1996).
GN Store Nord, "GN Store Nord Invests $12 Million in Ear Scanning Company," hearingreview.com (2012).
Goodwin, J., A Capsule Camera Instead of a Colonoscopy, Health, May 10, 2011, 2 pages.
Gorthi, S.S., et al., Fringe Projection Techniques: Whither we are? Optics and Lasers in Engineering, 48(2), pp. 133-140 (2010).
Grundfest, W., et al., "Real-Time Percutaneous Optical Imaging of Anatomical Structures in the Heart Through Blood Using a Catheter-Based Infrared Imaging System," Seminars in Thoracic and Cardiovascular Surgery, 19:336-341 (2007).
Honda, Y., et al., "Frontiers in Intravascular Imaging Technologies," Circulation, 117:2024-2037 (2008).
IVUS Imaging Products Overview, Volcano Precision Guided Therapy, www.volcanocorp.com/products/ivus-imaging, 2012, 1 page.
Knight, B., et al., "Direct Imaging of Transvenous Radiofrequency Cardiac Ablation Using a Steerable Fiberoptic Infrared Endoscope," Heart Rhythm, 2:1116-21 (2005).
Logozzo, S., et al., "Recent Advances in Dental Optics—Part I: 3D Intraoral Scanners for Restorative Dentistry," Optics and Lasers in Engineering, 54:203-221 (2014).
Lundqvist, C.B., et al., "The Use of Imaging for Electrophysiological and Devices Procedures: A Report from the First European Heart Rhythm Association Policy Conference, Jointly Organized with the European Association of Cardiovascular Imaging (EACVI), the Council of Cardiovascular Imaging and the European Society of Cardiac Radiology," Europace, 15:927-936 (2013).
Maier-Hein et al., "Optical Techniques for 3D Surface Reconstruction in Computer-Assisted Laparoscopic Surgery," Medical Image Analysis 17, pp. 974-996, available May 3, 2013 (2013).
Mozaffarian, D., et al., "Heart Disease and Stroke Statistics—2015 Update: A Report from the American Heart Association," Circulation, 131:e29-e322, e535 (2014).
Roger, V., et al., "Heart Disease and Stroke Statistics—2012 Update: A Report from the American Heart Association," Circulation, 125:e2-e220, e1002 (2011).
Roggan, A., et al., "Optical Properties of Circulating Human Blood," Part of the SPIE Conference on Optical Diagnostics of Biological Fluids III, SPIE vol. 3252, pp. 70-82 (1998).
Takeda, M., et al., Fourier Transform Profilometry for the Automatic Measurement of 3-D Object Shapes, Applied Optics, vol. 22, No. 24, pp. 3977-3982 (Dec. 1983).
Toennies et al., "Swallowable Medical Devices for Diagnosis and Surgery: the State of the Art," Proc. IMechE vol. 224 Part C: J. Mechanical Engineering Science, pp. 1397-1414, Dec. 9, 2009 (2009).
International Search Report and Written Opinion in PCT/US2014/023285, 12 pages, dated May 30, 2014.
International Search Report and Written Opinion in PCT/US2015/044636, 11 pages, dated Mar. 21, 2016.
International Search Report and Written Opinion in PCT/US2018/017839, 13 pages, dated Apr. 11, 2018.
Rocchini et al., "A low cost 3D scanner based on structured light," Eurographics, vol. 20(3) (2001).

* cited by examiner

100

200

300

400

500

600

700

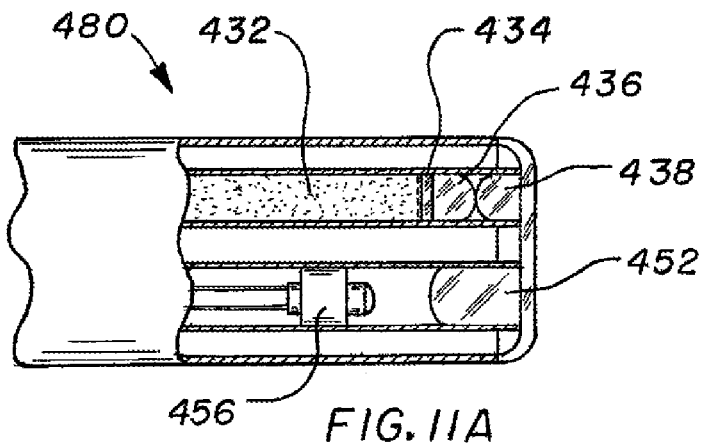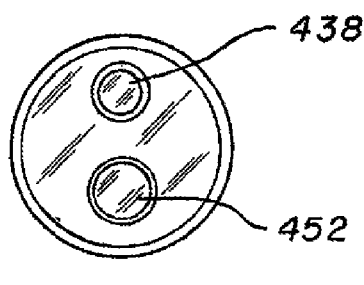
FIG. 11A          FIG. 11B
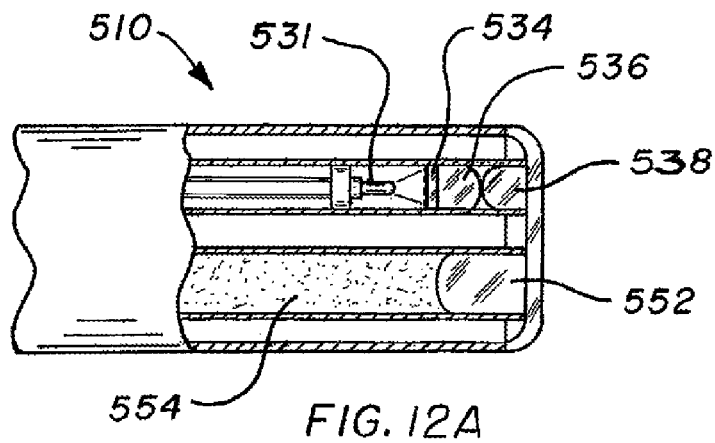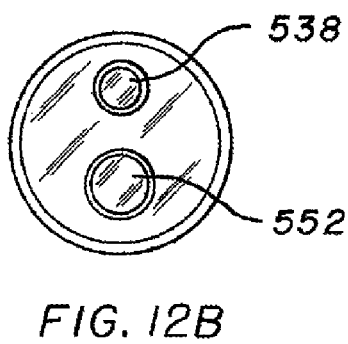
FIG. 12A          FIG. 12B
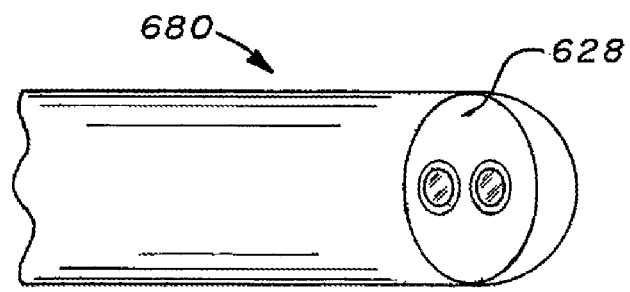
FIG. 13B
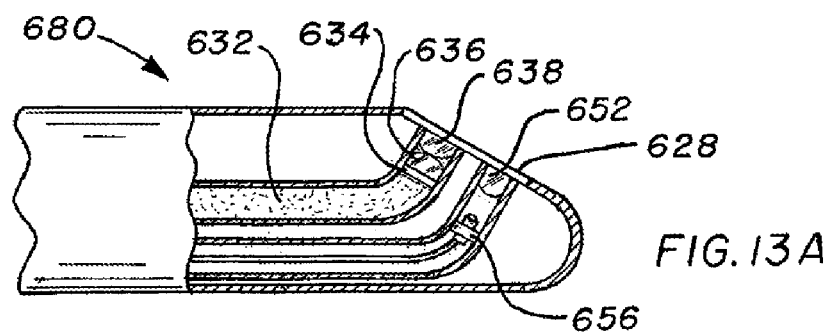
FIG. 13A

FULL-FIELD THREE-DIMENSIONAL SURFACE MEASUREMENT

CROSS-REFERENCE TO RELATED APPLICATIONS

This application is a continuation-in-part of U.S. patent application Ser. No. 15/252,685, filed Aug. 31, 2016, which is a continuation of U.S. patent application Ser. No. 13/830,477 filed Mar. 14, 2013. This application is also a continuation-in-part of U.S. patent application Ser. No. 15/894,567, filed Feb. 12, 2018, which claims the benefit of U.S. Provisional Patent Application No. 62/458,691, filed Feb. 14, 2017.

The entire contents of U.S. Patent Application Publication No. 2016/0367123, U.S. Patent Application Publication No. 2014/0276093, and U.S. Patent Application Publication No. 2018/0234600 are hereby incorporated herein by reference.

BACKGROUND

Accurate three-dimensional maps of external and internal human body surfaces are necessary for many medical procedures. For example, external body surfaces may need to be scanned for facial reconstructive surgery or the fitting of prosthetics. Internal body surfaces may need to be mapped for various endoscopic or catheter-based procedures, such as virtual biopsy, stenting, ablation, bronchoscopy, esophagogastroduodenoscopy, laparoscopy, colonoscopy, cystoscopy, or arthroscopy. Further, some internal procedures may take place in gaseous media, such as a bronchoscopy, and others may take place in liquid media, such as arthroscopy or cardiovascular visualization.

Current techniques for three-dimensional scanning external and internal body surfaces have many drawbacks. Laser-based scanning, such as a laser line scan, typically requires a patient to remain motionless, with even minor movements affecting the accuracy of the scan. A typical laser scan may require a patient to sit still for ten to fifteen seconds while many two-dimensional slices are gathered. The two-dimensional slices are later recompiled into a three-dimensional representation of a surface. Movement during this time period by the patient, including respiration, tremors, or muscle reflexes, can negatively impact the accuracy of the scan. Further, laser scanning equipment itself may introduce unwanted vibration into the system due to the inherent movement of the laser.

Commonly used techniques for internal organ measurements suffer from similar induced errors, these methods include computed tomography (CT), optical coherence tomography (OCT), magnetic resonance imaging (MRI), and various ultra-sound approaches (US and IVUS).

Thus, a need exists for three-dimensional surface measurement techniques that may be performed quickly and may eliminate inaccuracies introduced by patients and equipment.

Hearing aids are commonly used to assist hearing-impaired persons, enabling them to hear sounds that they otherwise would not be able to hear. Many different types of hearing aids are available. Many hearing aids are designed such that all or part of the hearing aid fits in the outer ear cavity and/or inside the ear canal.

In order to get a good fit of the hearing aid, hearing aids are commonly custom made. Typically, an impression is made of the patient's outer ear cavity and/or ear canal, depending on the type of hearing aid desired. The impression is made by filling the desired area of the outer ear and/or ear canal with a quick-setting material, often a silicone material, allowing the material to set by curing in the ear. Once set, the impression is withdrawn, and an earmold for the hearing aid is made based on the impression.

The impression process has a number of potential drawbacks. For example, the process can be time-consuming, can cause patient discomfort, can cause patient anxiety, and can be expensive. The impression process can also cause damage to the ear and may not be suitable for measurements far into the ear canal and/or to the eardrum. The impression can be inaccurate, leading to a poor-fitting earmold. If the impression is of poor quality, the process may need to be repeated. In addition, the ear canal is typically dynamic, having different shapes depending on different jaw positions. This can be particularly problematic with patients with large temporomandibular (TMJ) joint movement that can affect the ear canal. It can be difficult and time-consuming to take multiple impressions, each representing a different jaw position.

A need exists for an improved system and method for modeling an ear canal.

SUMMARY OF THE INVENTION

The disclosure provides systems and methods that may be used to perform measurement of surfaces, such as external and internal surfaces of the human body, in full-field and in 3-D. Embodiments of the present invention may be configured to project electromagnetic radiation onto a surface in a pattern. An image sensor may be configured to capture image data representing reflections of the projected pattern. An image-processing module may be configured to receive the captured image data from the image sensor and to calculate a full-field, 3-D representation of the surface using the captured image data and a spatial signal modulation algorithm. A display device may be configured to display the full-field, 3-D representation of the surface.

The disclosure also provides various systems and methods for making a three-dimensional model of the inside of an ear canal. Such a model is useful, for example, for manufacturing an earmold, such as for a hearing aid, to fit inside the ear canal.

One example of a system comprises an instrument having a probe adapted to be inserted into the ear canal. The probe comprises a narrow portion adapted to fit inside the ear canal and a wide portion adapted to be wider than the ear canal, the wide portion acting as a stop to limit the distance of the narrow portion of the probe into the ear canal. The narrow portion of the probe carries at least the distal end of an illumination subsystem and the distal end of an imaging subsystem. The wide portion of the probe may be formed by a tapered stop that is narrower at an end facing the ear canal and wider at an end facing away from the ear canal.

The illumination subsystem may comprise a light source, a pattern screen, and a lens, with at least the lens being located in a distal end of the probe. The illumination subsystem is adapted to project light from the light source, through the pattern screen, and through the lens in order to project a pattern of light from the distal end of the probe onto a surface of the ear canal, the pattern being modulated by the three-dimensional surface of the ear canal. The imaging subsystem comprises a video camera and a lens, with at least the lens being located in the distal end of the probe. The imaging subsystem is adapted to capture in succession, at a video frame rate of the video camera, a plurality of individual images of the pattern of light projected onto the surface of the ear canal, each individual image corresponding to a video frame.

An example system may also comprise a computer subsystem adapted to calculate an individual digital three-dimensional representation from each individual image in the plurality of individual images. The computer subsystem may use a spatial signal modulation algorithm to perform the calculations. The calculations result in a plurality of individual digital three-dimensional representations of the imaged surface. The computer subsystem is also adapted to stitch together the individual digital three-dimensional representations to generate a digital three-dimensional model of the ear canal.

In one example, the illumination subsystem projects light only in a range of 10 nm to 550 nm. Alternatively, the illumination subsystem may project only green light, only blue light, or only ultraviolet light. The pattern screen may comprise a grating of alternating opaque and transparent stripes. The lens of the imaging subsystem may be a wide-angle lens that enables the video camera to capture in one image up to a full 180-degree view of the ear canal.

In an example method of making a three-dimensional model of the inside of an ear canal, the method comprises: inserting a probe into the ear canal, the probe carrying at least a distal end of an illumination subsystem and at least a distal end of an imaging subsystem; projecting light from the light source, through the pattern screen, and through the lens of the illumination subsystem, and thereby projecting a pattern of light from the distal end of the probe onto a surface of the ear canal, the pattern being modulated by the three-dimensional surface of the ear canal; capturing in succession, at a video frame rate of the video camera, a plurality of individual images of the pattern of light projected onto the surface of the ear canal, each individual image corresponding to a video frame; and calculating an individual digital three-dimensional representation from each individual image in the plurality of individual images, the calculations resulting in a plurality of individual digital three-dimensional representations, and stitching together the individual digital three-dimensional representations to generate a digital three-dimensional model of the ear canal.

BRIEF DESCRIPTION OF THE DRAWINGS

FIG. 11A shows another example of a distal end of an instrument, showing the distal tip of a probe in a partial cut-away view.

FIG. 11B shows an end view of the distal tip of the probe of FIG. 11A.

FIG. 12A shows another example of a distal end of an instrument, showing the distal tip of a probe in a partial cut-away view.

FIG. 12B shows an end view of the distal tip of the probe of FIG. 12A.

FIG. 13A shows another example of a distal end of an instrument, showing the distal tip of a probe in a partial cut-away view.

FIG. 13B shows a top view of the distal tip of the probe of FIG. 13A.

DETAILED DESCRIPTION

The present invention relates to real-time, full-field, three-dimensional ("3-D") surface replication. Embodiments of the present invention may be used to perform measurement of surfaces, such as external and internal surfaces of the human body, in full-field and in 3-D. Full-field may refer to the ability of a device's sensor to capture and compute 3-D information of an entire scene containing an object being measured, for example. Real-time may refer to use of sufficiently fast sensor exposures or frame rates to minimize or eliminate perceptible target surface motion, for example.

Embodiments of the present invention may include an electromagnetic radiation source, which may be configured to project electromagnetic radiation onto a surface. The electromagnetic radiation source may be configured to project the electromagnetic radiation in a pattern corresponding to a spatial signal modulation algorithm. The electromagnetic radiation source may also be configured to project the electromagnetic radiation at a frequency suitable for transmission through the media in which the radiation is projected. An image sensor may be configured to capture image data representing the projected pattern. An image-processing module may be configured to receive the captured image data from the image sensor and to calculate a full-field, 3-D representation of the surface using the captured image data and the spatial signal modulation algorithm. A display device may be configured to display the full-field, 3-D representation of the surface.

Embodiments of the present invention may be further integrated into a probe, diagnostic or therapeutic catheter, endoscope, or a capsule to allow full-field, 3-D surface replication on internal surfaces of the human body. Such a device may be internally or externally guided, steerable or propelled in order to be advanced to, or navigated through cavities or the cardiovascular system.

Figure 1:
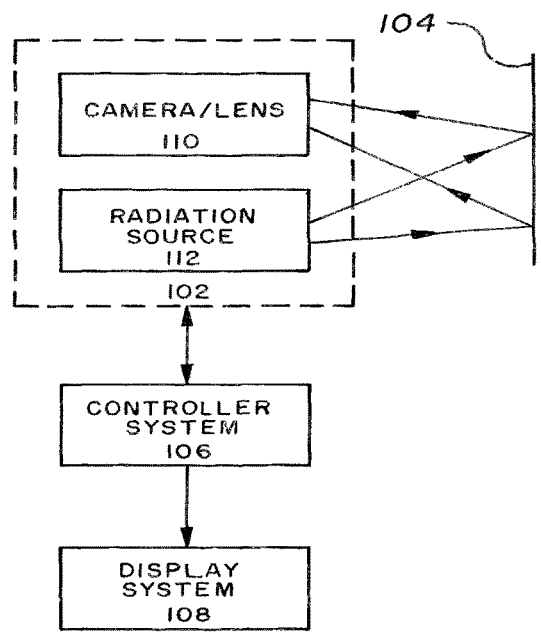
FIG. 1 illustrates an embodiment of the present invention.

FIG. 1 illustrates a real-time, full-field, 3-D surface replication system 100 according to embodiments of the present invention. System 100 may include a measurement package 102, a target surface 104, a controller system 106, and a display system 108. System 100 may implement the spatial signal modulation (SSM) techniques described in U.S. Pat. No. 5,581,352 filed on Feb. 27, 1995, the entirety of which is hereby incorporated by reference, to reproduce instant, quantifiable 3-D maps of external and internal surfaces of the human body.

Measurement package 102 may include a camera device 110 and a radiation source 112. The radiation source 112 may be fabricated by placing a slide or grating (not shown) with a desired pattern between a radiation emitting device and a lens (not shown). The camera device 110 may be a device capable of capturing image data reflected from the target surface 104 (e.g., a charge-coupled device (CCD) camera).

Controller system 106 (or image processing module) may include a processor or state machine capable of receiving image data captured by the camera device 110 and processing the data to calculate a full-field, 3-D representation of the target surface 104. Such a machine may include, for example, any suitable processing platform, computing platform, computing device, processing device, computing system, processing system, computer, processor, or the like, and may be implemented using any suitable combination of hardware and/or software.

Display system 108 may include a display device (liquid crystal display device, light emitting diode display device, etc.) to receive the full-field, 3-D representation of target surface 104 from the controller system 106 and display the digital representation of the surface 104 to be analyzed by a user.

Figure 2:
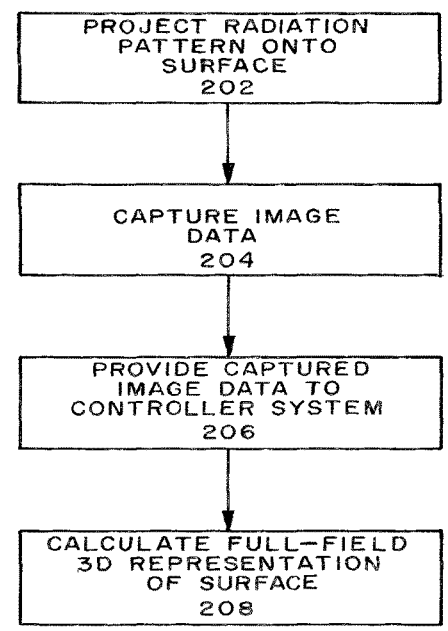
FIG. 2 illustrates a logic flow according to an embodiment of the present invention.

FIG. 2 is a logic flow 200 of an operation of the replication system 100 of FIG. 1 according to embodiments of the present invention. During operation, radiation source 112 may project a pattern of electromagnetic radiation, according to a spatial signal modulation algorithm, onto a target surface 104 (step 202). The pattern may take the appearance of parallel bands of electromagnetic radiation, for example. According to embodiments of the present invention, the carrier frequency of the projected spatial radiation signals may depend on the media the signals are propagating through. For example, human blood is some 2,500 times more transparent at certain infrared frequencies versus shorter wavelengths in the visible blue range. It is also not possible to use electromagnetic radiation to "see" an object if the wavelength of the radiation used is larger than the object. Thus, the emitter carrier frequency may be chosen based upon one or more characteristics (particle size, color, quantity of particles, etc.) of a media (air, blood, mucus, urine, etc.) adjacent to a target surface.

The spatial signals may reflect from the target surface 104 back to the camera device 110. The camera device 110 may capture the reflected spatial signals, which are changed/modulated by interaction with the surface 104 (step 204). The captured reflection images of the distorted projections contain spatially encoded 3-D surface information. Data representing the reflected (and distorted) spatial signals may be transmitted to the controller system 106 for processing (step 206).

Controller system 106 may include an image processing module and may use existing information regarding various signal parameters to isolate the content of the reflected spatial signal that contains the 3-D shape information. The shape information may be used to mathematically reconstruct the 3-D shape of target surface 104 (step 208). Controller system 106 may transmit digital data corresponding to the calculated representation of the surface 104 to the display system 108 to display a digital image representing a 3-D view of the surface 104.

Figure 3:
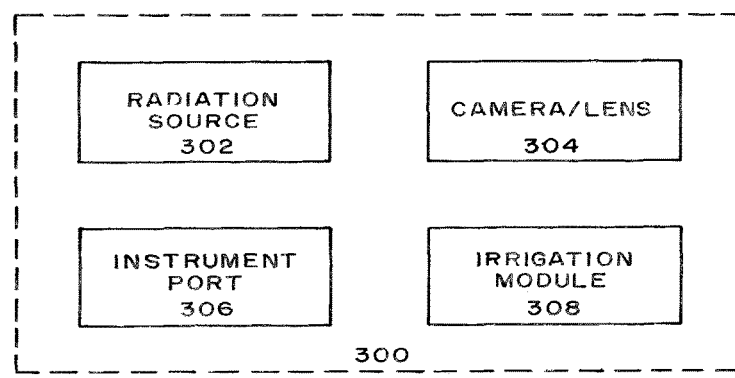
FIG. 3 illustrates a measurement package according to an embodiment of the present invention.

FIG. 3 illustrates a measurement package 300 according to embodiments of the present invention. Measurement package 300 may include a radiation source 302, a camera/lens device 304, an instrument port 306, and an irrigation module 308. Radiation source 302 and camera/lens device 304 (which are similar to radiation source 112 and camera device 110 in FIG. 1, respectively) are used to implement the SSM techniques described above.

Instrument port 306 may be a hollow tube that permits insertion of a wide array of surgical devices that may be interchanged during a procedure to fit the current needs of a physician. The irrigation module 308 may include a channel which introduces an inert fluid (e.g., saline) under pressure to clear debris off of the exterior of the camera/lens 304 during a procedure. Instrument port 306 and irrigation module 308 are optional features of measurement package 300.

Measurement package 300 may be implemented in a system (similar to system 100 of FIG. 1) to project radiation patterns with specific frequencies onto a surface, capture distorted reflections of the radiation pattern, and process the distorted reflections to facilitate analysis by an array of mathematical processes to reconstruct a 3-D shape of the surface. Embodiments of the present invention may integrate variations of measurement package 300 into medical devices to generate 3-D representations of various surfaces. For example, embodiments of the present invention may be used to generate 3-D representations of external human surfaces (e.g., faces, hands, feet, etc.). Embodiments of the present invention may also be used to generate 3-D representations of internal human surfaces (e.g., heart chambers, lungs, intestines, etc.).

Figure 4A:
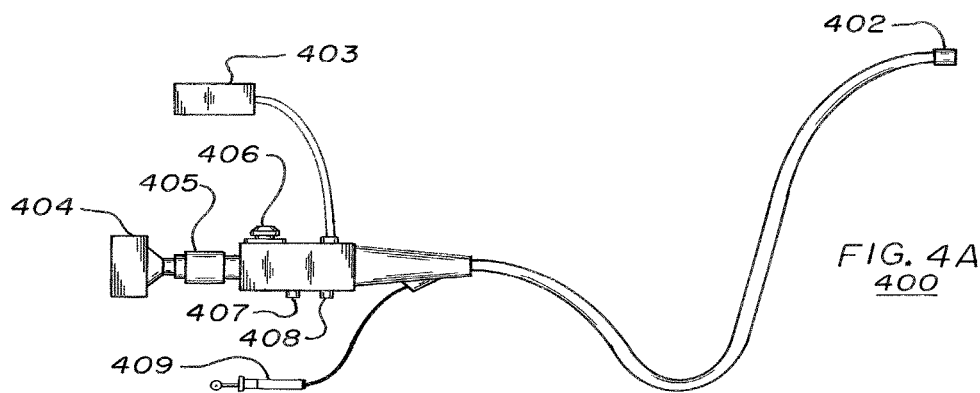
FIG. 4A illustrates an endoscope according to an embodiment of the present invention.
Figure 4B:
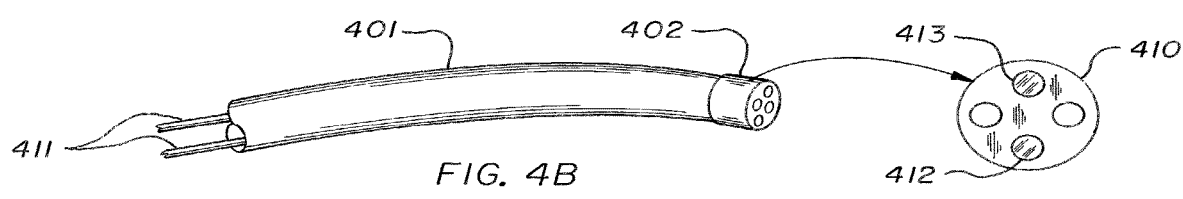
FIG. 4B illustrates an endoscope according to an embodiment of the present invention.
Figure 4C:
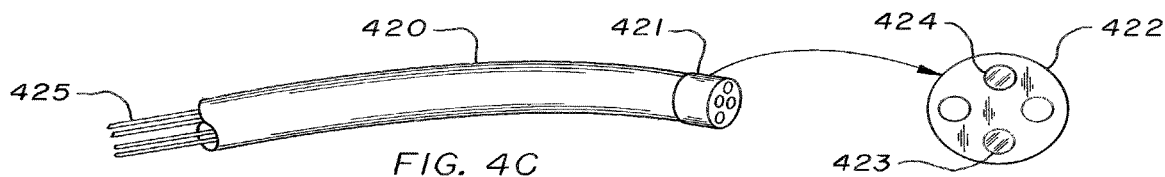
FIG. 4C illustrates an endoscope according to an embodiment of the present invention.

FIGS. 4A-C illustrate variations of endoscopes according to embodiments of the present invention. Referring to FIG. 4A, endoscope 400 may be used to examine interiors of internal human organs/cavities and generate full-field, 3-D representations of the organs/cavities. Endoscope 400 may include a catheter section 401, a distal end 402, a camera 404 (similar to camera 110 of FIG. 1), and a radiation source 403 (similar to radiation source 112 of FIG. 1). The camera 404 and radiation source 403 may be connected to the catheter section 401 on one end of the catheter section 401 and the distal end 402 may be connected to the catheter section 401 on another end of the catheter section 401. In other embodiments, the camera 404 and radiation source 403 may both be located at the end of catheter section 401 opposite distal end 402, the camera 404 and radiation source 403 may both be located at the end of catheter section 401 at distal end 402, or the camera 404 and radiation source 403 may be located at opposite ends of catheter section 401.

Catheter section 401 may be a flexible shaft and may include a number of channels (not shown) which may facilitate an examination of a patient's body. The channels in the catheter section 401 may run from one end of the catheter 401 to another end to allow transmission of data between camera 404/radiation source 403 and distal end 402 (described in further detail below). The channels may permit a physician to engage in remote operations such as transmission of images captured by the distal end 402, providing radiation generated by the radiation source 403 to distal end 402, irrigation for washing and removing debris from distal end 402 (using air/water pathway 407 and suction pathway 408), and introduction of medical instruments into a patient (via instrument pathway 409).

Operation of an endoscope according to an embodiment of the present invention will now be described with respect to FIGS. 4A and 4B. FIG. 4B illustrates a detailed view of catheter section 401 of endoscope 400 according to an embodiment of the present invention. Cather section 401 may include distal end 402 and a fiber optics bundle 411. Distal end 402 may include a distal tip 410 with projection optics 412 and imaging optics 413. The projections optics 412 and imaging optics 413 may each include a lens to focus the radiation used by the endoscope 400. Lenses may be used to focus radiation, and may include optical lenses, parabolic reflectors, or antennas, for example. Fiber optics bundle 411 may connect radiation source 403 to projection optics 412 to facilitate transmission of electromagnetic radiation from radiation source 403 to projection optics 412. Fiber optics bundle 411 may also connect camera 404 to imaging optics 413 to facilitate transmission of imaging data captured by imaging optics 413 to camera 404.

Endoscope 400 may generate full-field, 3-D representations of internal human organs and cavities using the SSM techniques described above with respect to FIGS. 1-3. During an operation, distal end 402 and catheter shaft 401 may be inserted into a patient and guided to a surface inside the patient's body that is under examination. Once the distal end 402 is properly oriented, the radiation source 403 may transmit a spatial pattern of electromagnetic radiation to projection optics 412 via fiber optics bundle 411. As described above with respect to FIGS. 1-3, the frequency of the electromagnetic radiation may be modified depending on the media (the area between the distal tip 410 and the target surface) the radiation is propagating through. The pattern of electromagnetic radiation may be projected onto the surface under examination by placing a slide or grating (not shown) with a desired pattern between the radiation source 403 and the fiber optics bundle 411 in the catheter section 401. The pattern of electromagnetic radiation may propagate through the fiber optics bundle 411, exit through projection optics 412 at the distal tip 410, and project onto the target surface.

The spatial radiation signals may reflect from the target surface back to the distal tip 410 and imaging optics 413 may capture the reflected signals (which are modulated by interaction with the surface). The captured reflection images may be transmitted from imaging optics 413 to camera 404 via fiber optics bundle 411 and subsequently transmitted to a controller system (not shown, but similar to controller system 106 of FIG. 1). The controller system may use existing information regarding various signal parameters to isolate the content of the reflected spatial signal that contains the 3-D shape information. The shape information may be used to mathematically reconstruct the 3-D shape of target surface.

Moreover, endoscope 400 may be used to construct full-field surface maps of long passageways in a patient's body (e.g., gastrointestinal passageways) by moving the endoscope 400 through a given passageway. While endoscope 400 is being guided through a given passageway, continuous full-field surface maps may be generated by stitching together the 3-D data gathered during each video frame captured by camera 404. The 3-D data may be stitched together using algorithms known in the art implemented in software, hardware, or a combination of software and hardware. In this manner, an accurate 3-D model of the cavity in which the device is traveling may be constantly digitally developed and recorded. Thus, embodiments of the present invention may provide a continuous real-time, 3-D representation of the interior of a patient's gastrointestinal passageways. Such methods may also be used for other internal organs that may not be captured by a stationary endoscope.

FIG. 4C illustrates another embodiment of a catheter section 420 with a distal end 421 and electrical and data leads 425 in accordance with the present invention. Distal end 421 may include a distal tip 422 with imaging optics 424 (similar to imaging optics 413 in FIG. 4B) and electromagnetic radiation emitter 423. Electromagnetic radiation emitter 423 may be molded onto distal tip 422 and may project the spatial radiation signals (similar to the signals described above with respect to FIGS. 1-4B). Emitter 423 may contain a lamp, a pattern slide, and a lens (not shown, but described in FIG. 5 below) and may project a spatial pattern onto a target surface when power is provided to it via electrical and data leads 425. Thus, there is no need for an external electromagnetic radiation source (similar to source 403 in FIG. 4) because emitter 423 may be capable of locally generating radiation patterns and projecting them onto target surfaces.

Catheter section 420 may be utilized alone, integrated into, or passed through the working lumen of an endoscopic device (similar to endoscope 400 of FIG. 4A, but possibly without the radiation source 403) and may utilize the SSM techniques described above. During operation, emitter 423 may receive power via electrical and data leads 425 and subsequently project a spatial electromagnetic radiation pattern onto a target surface according to a spatial signal modulation algorithm. The frequency of the electromagnetic radiation used to project the spatial pattern may be modified depending on the media which the radiation is propagating through (as previously described).

The spatial radiation signals may reflect from the target surface back to the distal tip 422 and imaging optics 424 may capture the reflected signals (which are modulated by interaction with the surface). The captured reflection images may be transmitted from imaging optics 424 to a camera (not shown, but similar to camera 404 in FIG. 4A) via electrical and data leads 425 and subsequently transmitted to a controller system (not shown, but similar to controller system 106 of FIG. 1). The controller system may use existing information regarding various signal parameters to isolate the content of the reflected spatial signal that contains the 3-D shape information. The shape information may be used to mathematically reconstruct the 3-D shape of target surface.

Embodiments of the present invention integrating the catheter section 420 with distal end 421 into an endoscopic device may also be used to construct full-field surface maps of long passageways in a patient's body (e.g., gastrointestinal passageways) by moving the endoscope through a given passageway (similar to the embodiment described with respect to FIGS. 4A-B). While the endoscope is being guided through a given passageway, continuous full-field surface maps may be generated by stitching together the 3-D information calculated from information contained in each video frame captured by the camera.

Figure 5:
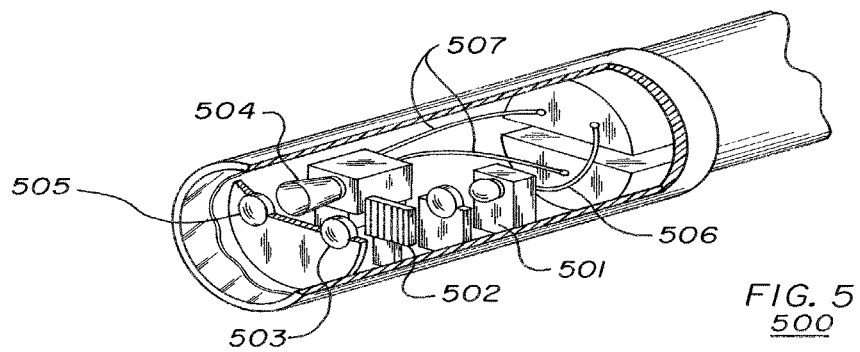
FIG. 5 illustrates a distal end according to an embodiment of the present invention.

FIG. 5 illustrates a detailed, cross-sectional view of a distal end 500 that may be integrated with an endoscope described above with respect to FIG. 4C according to an embodiment of the present invention. Distal end 500 may include a lamp 501, a pattern slide 502, an illumination lens 503, an imaging sensor 504, and an imaging lens 505.

Lamp 501, pattern slide 502, and illumination lens 503 may form an electromagnetic radiation emitter (not specifically labeled, but similar to emitter 423 in FIG. 4C) capable of projecting patterns of radiation onto a target surface according to a spatial signal modulation algorithm. The frequency of the electromagnetic radiation used to project the spatial pattern may be modified depending on the media which the radiation is propagating through (as previously described). During operation, lamp 501 may receive power from a power source (not shown) via electrical lead 506 and project electromagnetic radiation through pattern slide 502 and illumination lens 503 onto a target surface.

The spatial radiation signals may reflect from the target surface back to the distal end 500 through imaging lens 505, and imaging sensor 504 may capture the reflected signals (which are modulated by interaction with the surface). The captured reflection images may be transmitted from imaging sensor 504 via data leads 507 to a controller system (not shown, but similar to controller system 106 of FIG. 1). The controller system may use existing information regarding various signal parameters to isolate the content of the reflected spatial signal that contains the 3-D shape information. The shape information may be used to mathematically reconstruct the 3-D shape of target surface.

Figure 6:
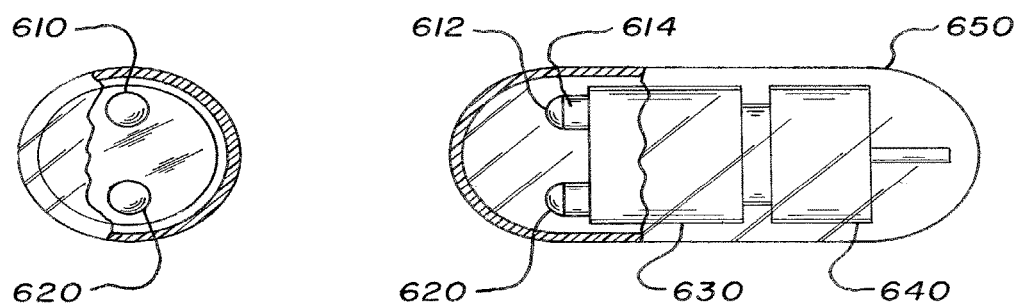
FIG. 6 illustrates a capsule according to an embodiment of the present invention.

FIG. 6 illustrates an endoscopic capsule 600 according to an embodiment of the present invention. FIG. 6 includes a cross-sectional view (on the left) and an overhead view (to the right) of capsule 600. Capsule 600 may be a small vitamin pill sized capsule that is capable of being ingested by a patient. The capsule 600 may implement the SSM techniques described above to generate full-field, 3-D representations of surfaces of a human digestive tract that are difficult to reach through traditional endoscopic examination.

Capsule 600 may include an imaging package 610, an electromagnetic radiation package 620, power supply and electronics 630, a wireless transmitter 640, and a transparent protective cover 650. The cover 650 may be an outer shell capable of protecting the devices in capsule 600 while it is flowing through the digestive tract of a patient. Imaging package 610 may include imaging optics 612 (e.g., a lens) and imaging sensor 614.

Capsule 600 may operate in a similar fashion to the embodiments described above, however, capsule 600 may be powered locally via power supply and electronics 630, which may include a battery, for example. Moreover, capsule 600 may transmit captured image data to an image processing module (not shown, but similar to controller system 106 of FIG. 1) located external to a patient's body using wireless transmitter 640. An antenna module (not shown) may be placed on the skin of the patient to facilitate data transmission from the capsule to the image processing module.

During operation, a patient may ingest capsule 600, which travels through the patient's digestive tract for measurement purposes. While capsule 600 is traveling through the patient's digestive tract, electromagnetic radiation package 620 (which may include an emitter that is similar to the electromagnetic radiation emitter 423 of FIG. 4C) may be powered by power supply and electronics 630 to constantly project spatial electromagnetic radiation patterns on surfaces in its path. The frequency of the electromagnetic radiation used to project the spatial pattern may be modified depending on the media (e.g., visible frequency transparent gases and clear fluids) which the radiation is propagating through (as previously described).

The spatial radiation signals may reflect from the target surface back to the imaging optics (the signals may be modulated by interaction with the surface). Image sensor 614 may capture the reflected images and transmit them, via wireless interface 640, from the capsule 600 to an image processing module (now shown, but similar to controller system 106 of FIG. 1). The image processing module may use existing information regarding various signal parameters to isolate the content of the reflected spatial signal that contains the 3-D shape information. The shape information may be used to mathematically reconstruct the 3-D shape of the target surface.

Reflection images captured by capsule 600 may be used to construct full-field surface maps of a patient's digestive tract as the capsule 600 is traveling in the tract by stitching together the 3-D data gathered during each video frame captured by image sensor 614. In this manner, an accurate 3-D model of the cavity in which the device is traveling may be constantly digitally developed and recorded. Capsule 600 may be generally moved along involuntarily by peristalsis or selectively propelled/guided electromagnetically.

Figure 7A:
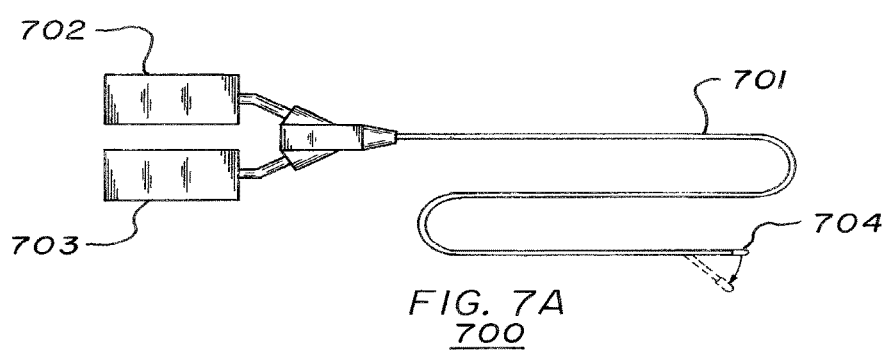
FIG. 7A illustrates a catheterization probe according to an embodiment of the present invention.
Figure 7B:
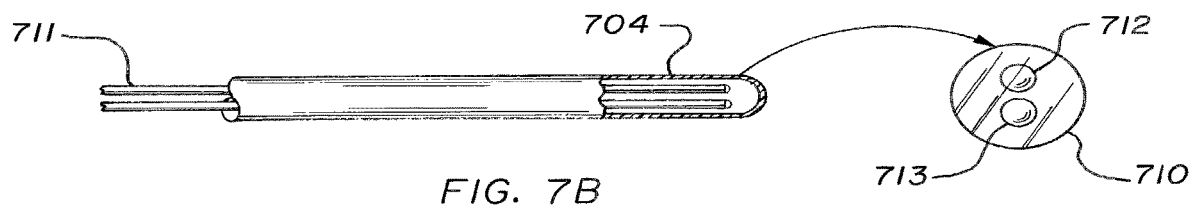
FIG. 7B illustrates a catheterization probe according to an embodiment of the present invention.

FIGS. 7A and 7B illustrate two views of a catheterization probe 700 according to an embodiment of the present invention. The probe 700 may be employed during a catheterization procedure to quantitatively examine structures during normal function or, for example, to detect and measure plaques and blockages in the coronary arteries. The catheterization probe 700 may include a catheter section 701, a radiation source 702 (similar to radiation source 403 of FIG. 4A), a radiation sensor 703, and a distal end 704. The radiation source 702 and the radiation sensor 703 may be connected to the catheter section 701 on one end of the catheter section 701, and the distal end 704 may be connected to the catheter section 701 on the other end of the catheter section 701. In other embodiments, radiation source 702 and the radiation sensor 703 may both be located at the end of catheter section 701 opposite distal end 704, radiation source 702 and the radiation sensor 703 may both be located at the end of catheter section 701 at distal end 704, or radiation source 702 and the radiation sensor 703 may be located at opposite ends of catheter section 701.

Catheter section 701 may be a flexible shaft and may include a fiber optics bundle 711 and a distal end 704. The distal end 704 may include a distal tip 710 with projections optics 712 and imaging optics 713. The projections optics 712 and imaging optics 713 may each include a lens to focus the radiation used by the probe 700. Fiber optics bundle 711 may connect radiation source 702 to the projection optics 712 to facilitate transmission of electromagnetic radiation from radiation source 702 to projection optics 712. Fiber optics bundle 711 may also connect radiation sensor 703 to imaging optics 713 to facilitate transmission of imaging data captured by imaging optics 713 to radiation sensor 703.

Catheterization probe 700 may generate full-field, 3-D representations of vascular anatomy such as heart valves, coronary arteries, or peripheral vasculature using the SSM techniques described above with respect to FIGS. 1-6. During a procedure the long, thin, and flexible shaft of the catheter section 701 may be introduced into a blood vessel and threaded into the target vessels of the heart. The probe 700 may have sufficient torsional rigidity and a deflectable portion at the distal end 704 (show in FIG. 7A) to facilitate torque steering as it is advanced within a cardiovascular environment.

Once the distal end 704 is properly oriented, the radiation source 702 may transmit a spatial pattern of electromagnetic radiation to projection optics 712 via fiber optics bundle 711. As described above with respect to FIGS. 1-6, the frequency of the electromagnetic radiation may be modified depending on the media (the area between the distal tip 710 and the target surface) the radiation is propagating through. The pattern of electromagnetic radiation may be projected onto the surface under examination by placing a slide or grating (not shown) with a desired pattern between the radiation source 702 and the fiber optics bundle 711 in the catheter section 701. The pattern of electromagnetic radiation may propagate through the fiber optics bundle 711, exit through projection optics 712 at the distal tip 710, and project onto the target surface.

The spatial radiation signals may reflect from the target surface back to the distal tip 710 and imaging optics 713 may capture the reflected signals (which are modulated by interaction with the surface). The captured reflection images may be transmitted from imaging optics 713 to radiation sensor 703 via fiber optics bundle 711 and subsequently transmitted to a controller system (not shown, but similar to controller system 106 of FIG. 1). The controller system may use existing information regarding various signal parameters to isolate the content of the reflected spatial signal that contains the 3-D shape information. The shape information may be used to mathematically reconstruct the 3-D shape of target surface.

In this manner, full field digital 3-D surface maps of cardiac cavities may be continuously generated by the measurement package (projection optics 712 and imaging optics 713) located at the distal tip 710 of the probe 700. These computer-generated maps combine to form a virtual environment of the interior surface of the cavity under study. This information may be presented on a display device, either locally to the attending operating room staff, or transmitted remotely, creating a telepresence for diagnosis by an expert located remotely from the patient. The real-time 3-D model information may be used as a navigational aid within the vessel, tracking and recording progress and surface structures. Once within the vascular or cardiac structures, the distal tip 710 may be navigated to the area of interest and may provide accurate, direct, and quantitative 3-D observation of a functioning anatomy.

Embodiments of the present invention described above provide devices and methods to generate accurate, high-speed 3-D surface representations. By carefully varying the frequency of the radiation projected onto target surfaces, physicians may be able to see through media that were previously considered opaque. Tailoring emitter-sensor packages to specific frequencies depending on the media the radiation is traveling through allows reproduction of 3-D surfaces both internal and external to the human body.

Moreover, integrating the SSM techniques described above with medical devices such as probes, endoscopes, catheters, or capsules may enable physicians to generate accurate full-field, 3-D representations of surfaces that were previously very difficult to produce. The medical applications of in-vivo topometric data are innumerable. Internal real-time 3-D sensing applied through endoscopic or catheter-based inspection of gastrointestinal, cardiovascular, or bronchial passageways may assist detection of anomalous structures, constrictions, or growths. Devices and methods in accordance with the embodiments of the present invention described above may be invaluable for virtual biopsies and early detection in oncology as many cancers may originate on surfaces of the internal anatomy. Catheter based, quantifiable 3-D mapping of plaque strictures in coronary arteries may allow for better diagnosis of heart disease and placement of stents or other appliances. There are numerous other medical applications for the techniques and devices described above.

In an example, a system for making an earmold for a hearing aid comprises a system for generating a three-dimensional model of an ear canal of a human or animal patient and a system for manufacturing an earmold using that three-dimensional model. The system for generating the three-dimensional model of the ear canal uses spatial signal modulation (SSM) to determine the dimensions of the ear canal for anatomical surface modeling. The spatial signal modulation apparatus may utilize projection and image-capturing optics co-located at the distal tip of a probe. The model of the ear canal may be a model of all or only a portion of the ear canal, and it may include modeling of all or part of the eardrum (tympanic membrane) and/or all or part of the outer ear.

In this example, a system for generating the three-dimensional model of the ear canal comprises a probe, an illumination subsystem for projecting a light pattern onto the surface of the ear canal, and an imaging subsystem for capturing a series of individual images, each individual image being an image of a part the ear canal surface with the light pattern projected onto it, the light pattern being deformed or modulated by the contours of the surface. The system for generating the three-dimensional model of the ear canal further comprises a computer subsystem running software comprising a spatial signal modulation algorithm for converting each individual image in the series of images into an individual digital point cloud, each individual digital point cloud representing a three-dimensional model of a part the ear canal surface, and a stitching algorithm for stitching together the individual digital point clouds into an overall digital point cloud, the overall digital point cloud representing a three-dimensional model of the ear canal.

A system for manufacturing an earmold using the three-dimensional model of the ear canal may comprise a three-dimensional printer that prints the earmold based upon the three-dimensional model of the ear canal. In an alternative, a system for manufacturing an earmold using the three-dimensional model of the ear canal may comprise a three-dimensional printer that prints a mold for making the earmold based upon the three-dimensional model of the ear canal. Then the earmold is molded from that printed mold. In another alternative, a system for manufacturing an earmold using the three-dimensional model of the ear canal may comprise a three-dimensional printer that prints a part in the shape of the desired earmold based upon the three-dimensional model of the ear canal. Then, the printed part is used to make a mold for the earmold, and the earmold is molded from that mold. Alternatively, the earmold is thermoformed using the printed part. In another alternative, a system for manufacturing an earmold using the three-dimensional model of the ear canal may comprise machining or otherwise manufacturing a mold based upon the three-dimensional model of the ear canal and then molding the earmold using that mold.

In an example system for generating the three-dimensional model of the ear canal, the probe is adapted to allow a distal tip of the probe to be inserted into the ear canal and moved therein in order to obtain the series of images. The probe generally has a narrow portion that can fit inside the ear canal and a wide portion that cannot fit inside the ear canal. The probe may include a tapered stop that is narrower at one end than the other end. In such a case, the narrow portion of the probe may be a tube connected to the narrower end of the tapered stop and/or the narrower end of the tapered stop itself, and the wide portion of the probe may be the wider end of the tapered stop and/or a part connected to the wider end of the tapered stop. The tapered stop can have any suitable shape gradually transitioning from a narrower end to a wider end, for example conical, frustoconical, or curved or parabolic versions of such shapes. The wide portion of the probe acts as a stop that prevents the narrow portion of the probe from being inserted too far into the ear canal, so as to prevent damage to the eardrum or other injury.

Figure 8:
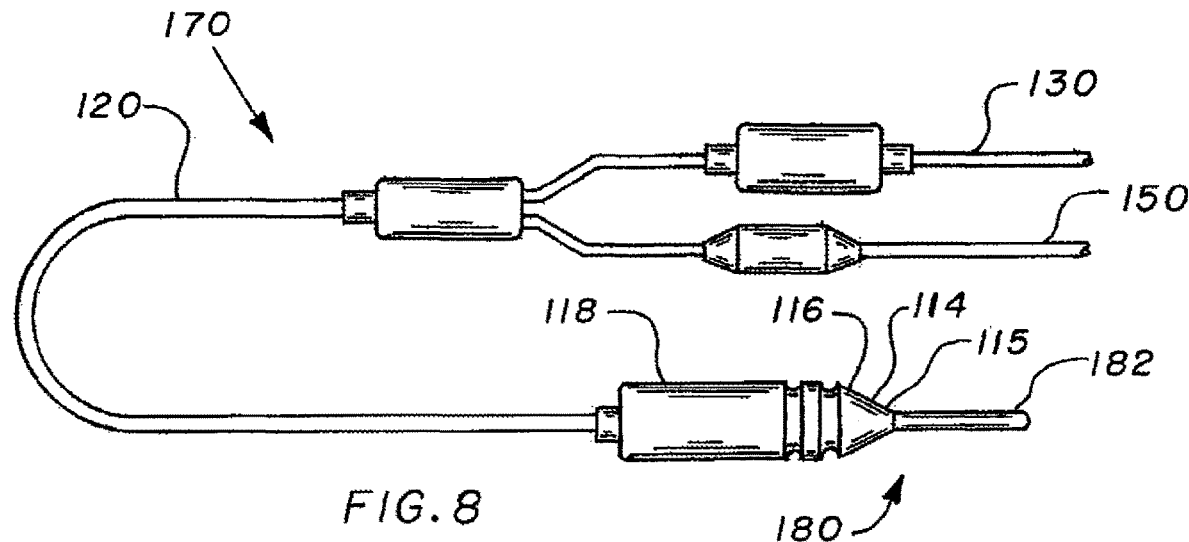
FIG. 8 illustrates an instrument that is a component of a system for generating a three-dimensional model of an ear canal.

FIG. 8 illustrates an instrument 170 that is a component of a system for generating a three-dimensional model of the ear canal. The instrument 170 carries projection and imaging optics for distal projection and image capture. The instrument 170 comprises a probe 180 at its distal end. The probe 180 has a narrow portion in the form of a rigid or semi-rigid tube 182 at its distal end. The probe 180 include a tapered stop 114 that is narrower at one end 115 than the other end 116. The tube 182 is connected to the narrower end 115 of the tapered stop 114. The wider end 116 of the tapered stop 114 forms the wide portion of the probe 180. The wider end 116 is connected to generally cylindrical portion 118, which can act as a grip or handle. The tapered stop 114 is oriented so that its narrower end 115 faces the tube 182 and thus faces toward the ear. The narrow portion or tube 182 can fit inside the ear canal, while the wide portion or wider end 116 of the tapered stop 114 cannot fit inside the ear canal. Thus, the wide portion of the probe, and in particular the wider end 116 of the tapered stop 114, acts as a stop that prevents the narrow portion of the probe from being inserted too far into the ear canal, so as to prevent damage to the eardrum or other injury. The grip or handle 118 may have one or more grip features, such as one or more grooves or notches or indents, to facilitate handling and manipulation of the probe. A user can hold the grip or handle 118 of the probe and maneuver the tube 182 of the probe within and around the ear canal to get multiple ear canal views, as described below.

The instrument 170 further comprises a flexible tube 120, an illumination subsystem branch 130, and an imaging subsystem branch 150. The instrument 170 houses components of the illumination subsystem and the imaging subsystem.

Figure 9A:
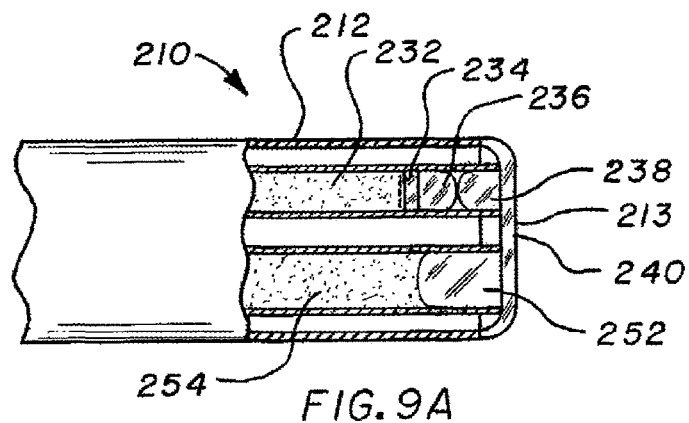
FIG. 9A shows an example of a distal end of an instrument, showing the distal tip of a probe in a partial cut-away view.
Figure 9B:
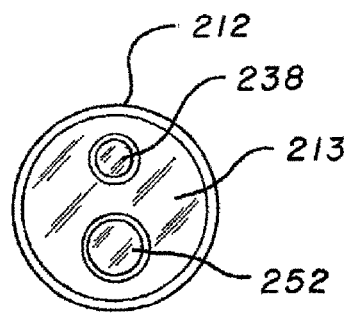
FIG. 9B shows an end view of the distal tip of the probe of FIG. 9A.

FIG. 9A shows an example of a distal end of an instrument, showing the distal tip of a probe 210 in a partial cut-away view. FIG. 9B shows an end view of the distal tip of the probe 210. In this example, the illumination subsystem comprises a light source (not shown) at the proximal end of the instrument, an optical fiber 232, which may be a single optical fiber (with a solid core) or a bundle of optical fibers (which may be randomized or coherent), a pattern screen 234, a first lens 236, and a second lens 238. The optical fiber(s) 232 extends the length of the instrument from the light source to the components at the distal end of the instrument. When the light source is turned on, light travels from the light source, through the optical fiber(s) 232, through the pattern screen 234, through the lenses 236, 238, and is projected out of the distal end 240 of the probe.

The pattern screen 234 is a component that comprises or has on it a pattern of transparent and opaque areas. In one form, the pattern is a Ronchi grating of alternating opaque and transparent stripes. The spacing of the alternating stripes may be any suitable spacing, such as 10, 20, 30, 40, 50, or 60 opaque stripe pairs, or cycles, per millimeter. The pattern screen may be a sheet or thin plate of transparent material with the pattern printed, etched, deposited, or otherwise formed in it or on it. In one example, the pattern screen may be a thin plate of glass or mylar film with a pattern formed by vapor deposition of a chrome material or other suitable material. In the illustrated example, the pattern screen 234 has a grating on the side that faces the optical fiber(s) 232. The pattern screen 234 blocks the light in a pattern, so that the light exiting the pattern screen 234 is in that pattern. In this way, a light pattern is projected onto the target surface, which in this case is the surface of the ear canal. The three-dimensional contours of the target surface distort or modulate the projected light pattern in a way that provides information that is used by the system for three-dimensional calculations. For example, in the case of a grating such as a Ronchi grating, the grating is projected onto the target surface, with the alternating stripes distorted or modulated due to the contours of the surface.

The pattern screen is a fixed component. The pattern screen does not move within the instrument, and the pattern of the pattern screen is fixed, i.e., it is constant and does not change.

The lenses 236, 238 are designed for projecting the pattern of light from the pattern screen 234 onto the target surface. One or more lenses may be used. In this example, lens 236 has a flat surface at its proximal side and a convex surface at its distal side, and lens 238 has a convex surface at its proximal side and a flat surface at its distal side. The flat surface of lens 236 is adjacent to and abuts the pattern screen 234, while the convex surface of lens 236 is adjacent to and abuts the convex surface of lens 238. The flat surface of lens 238 faces outwardly from the distal end 240 of the probe. The lenses may be of the single or multiple element type with flat, spherical, aspherical, convex, or concave surfaces, or gradient index rod lenses (GRIN) capable of producing the desired field of view (FOV). Short or zero length back focus distances may be utilized to maximize light transmission through the pattern screen from the fiber and focus the image of the pattern to be projected. Fields of view (FOV) of up to 180-degrees are possible with FOV in the range of 90-degrees more readily available and with reduced edge aberrations. The lens(es) may be designed to project the light pattern onto the target surface in a defocused manner. For example, a pattern of alternating stripes of light may be defocused to form a sinusoidal pattern on the target surface. In an alternative, the lens(es) may be designed to project the light pattern onto the target surface in a focused manner.

The light source may be any suitable light source, including but not limited to laser light, halogen light, LED light, and/or incandescent light. As one example, a broad spectrum visible light source may be used, projecting white light. As another example, a single wavelength or narrow band of wavelengths of light may be projected.

The wavelength (or frequency) may tuned to the medium and surface being measured. The ear canal can present a moist environment, causing specular reflections and/or absorption of some wavelengths of light. The specular reflections and absorption of light by the skin cells can be moderated by proper selection of the wavelength of the carrier light. In the case of the ear canal, projecting a spatial signal through a gaseous media (air) onto epithelial cells, shorter wavelengths (green or blue to ultraviolet) can help to reduce or eliminate the effects of both specular reflections and absorption of light by the skin cells. Thus, for imaging in the ear canal, through air onto the skin surface of the ear canal, a shorter wavelength light may be advantageous, such as green light, blue light, violet light, and/or ultraviolet light. For imaging in the ear canal, light in a wavelength range of 10 nm to 550 nm may be advantageous; in particular, light in a wavelength range of 490 nm to 550 nm, 465 nm to 490 nm, 400 nm to 465 nm, and/or 10 nm to 400 nm (ultraviolet) may be advantageous.

In the example of FIGS. 9A and 9B, the imaging subsystem comprises a lens 252, an optical fiber bundle 254, and an image sensor or digital video camera (not shown) located at the proximal end of the instrument. The camera may be, for example, a CCD camera or a CMOS camera. In one example, the camera is a 1.3 million pixel CCD monochrome camera. Cameras with higher or lower resolutions may be used. The optical fiber bundle 254 is a coherent imaging optical fiber bundle that extends from the distal end of the instrument adjacent to the lens 252 to the digital video camera at the proximal end of the instrument in order the enable the digital video camera to capture digital images of the target surface. The lens 252 may have a convex surface facing the optical fiber bundle 254 and a flat surface facing outwardly from the distal end 240 of the probe. The lens 252 may be a wide-angle lens that enables the camera to capture in one image a full cross-section or up to a 180-degree view of the ear canal. Similar to the projection optics, the imaging lenses may be of the single or multiple element type with flat, spherical, aspherical, convex, or concave surfaces, or gradient index rod lenses (GRIN) capable of producing the desired FOV.

As the probe is moved to different views in the ear canal, the camera captures successive images of the light pattern that is projected on and modulated by the ear canal surface. The camera captures an image with each frame of the video. In the United States video cameras generally follow the National Television System Committee (NTSC) standard of 30 frames per second, while Europe and Asia follow the Phase Alternating Line (PAL) standard of 25 frames per second. Specialized video cameras with higher frame rates are available that enable more frames to be captured in a given time to better cover rapidly changing scenes or moving objects. Thus, the imaging subsystem is adapted for capturing a series of individual images, each individual image being an image of a part the ear canal surface with the light pattern projected onto it, the light pattern being deformed or modulated by the contours of the ear canal surface.

The distal components of the illumination subsystem (in this embodiment, the distal end of optical fiber(s) 232, the pattern screen 234, and the lenses 236, 238) and the distal components of the imaging subsystem (in this embodiment, the distal end of optical fiber bundle 254 and the lens 252) are housed within the probe 210. The probe 210 has a housing in the form of a tube 212, which in this example is a cylindrical tube, although other shapes are possible. The end of the probe 210 is covered by an end cap 213, with access areas (holes or transparent areas) for the lenses of the illumination and imaging subsystems.

Figure 10A:
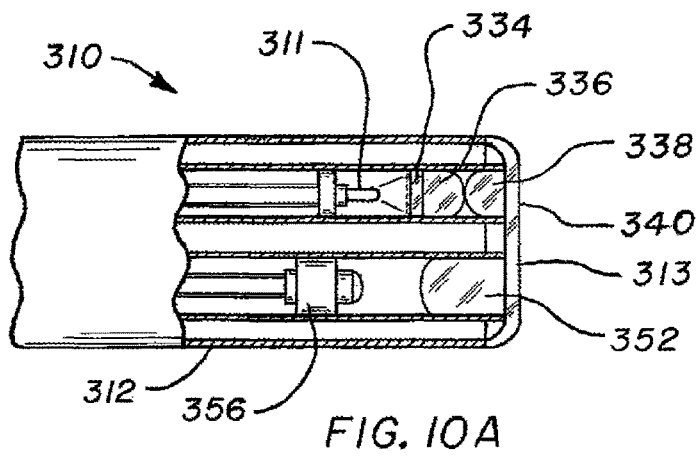
FIG. 10A shows another example of a distal end of an instrument, showing the distal tip of a probe in a partial cut-away view.
Figure 10B:
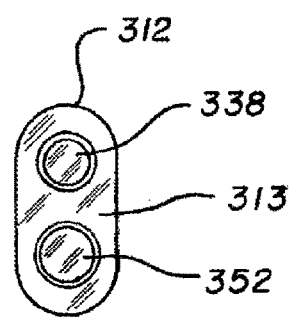
FIG. 10B shows an end view of the distal tip of the probe of FIG. 10A.

FIG. 10A shows another example of a distal end of an instrument, showing the distal tip of a probe 310 in a partial cut-away view. FIG. 10B shows an end view of the distal tip of the probe 310. In this example, the illumination subsystem comprises a light source 311 at the distal end of the instrument. Wiring for operation of the light source extends through the instrument and connects the light source to a power source. The illumination subsystem further comprises a pattern screen 334, a first lens 336, and a second lens 338, which may be similar to the pattern screen 234 and lenses 236, 238. When the light source 311 is turned on, light travels from the light source 311 through the pattern screen 334, through the lenses 336, 338, and is projected out of the distal end 340 of the probe. The light source, wavelength(s), and projected pattern may be similar in structure and function to those described above.

In FIGS. 10A and 10B, the imaging subsystem comprises a camera 356 at the distal end of the instrument (at the distal end of the probe), along with a lens 352. Placing the camera 356 at the distal end of the instrument and at the distal end of the probe can enable capturing of higher resolution images, since the coherent fiber optic bundle, which can limit resolution, may not be needed as part of the imaging subsystem in such an embodiment. The imaging subsystem operates in a similar manner as the imaging subsystem in FIGS. 9A and 9B. As the probe is moved to different views in the ear canal, the camera captures successive images of the light pattern that is projected on and modulated by the ear canal surface, capturing an image with each frame of video.

As with the embodiment of FIGS. 9A-9B, in the embodiment of FIGS. 10A-10B the distal components of the illumination subsystem (in this embodiment, the light source 311, the pattern screen 334, and the lenses 336, 338) and the distal components of the imaging subsystem (in this embodiment, the camera 356 and the lens 352) are housed within the probe 310. The probe 310 has a housing in the form of a tube 312, which in this example is has a cross-sectional shape in the form of a rectangle with semi-circles at opposite ends. Other shapes are possible, such as oval, rectangular with rounded corners, square with rounded corners, etc. The end of the probe 310 is covered by an end cap 313, with access areas (holes or transparent areas) for the lenses of the illumination and imaging subsystems.

FIG. 11A shows another example of a distal end of an instrument, showing the distal tip of a probe 480 in a partial cut-away view. FIG. 11B shows an end view of the distal tip of the probe 480. In this example, the illumination subsystem is similar in structure and function to that described above with respect to FIGS. 9A and 9B, and the imaging subsystem is similar in structure and function to that described above with respect to FIGS. 10A and 10B. The illumination subsystem comprises a light source (not shown) at the proximal end of the instrument, an optical fiber 432, a pattern screen 434, a first lens 436, and a second lens 438, similar in structure and function to the light source, optical fiber 232, pattern screen 234, first lens 236, and second lens 238 described above with respect to FIGS. 9A and 9B. The imaging subsystem comprises a lens 452 and a camera 456 at the distal end of the instrument, similar in structure and function to the lens 352 and camera 356 described above with respect to FIGS. 10A and 10B.

FIG. 12A shows another example of a distal end of an instrument, showing the distal tip of a probe 510 in a partial cut-away view. FIG. 12B shows an end view of the distal tip of the probe 510. In this example, the illumination subsystem is similar in structure and function to that described above with respect to FIGS. 10A and 10B, and the imaging subsystem is similar in structure and function to that described above with respect to FIGS. 9A and 9B. The illumination subsystem comprises a light source 531 at the distal end of the instrument, a pattern screen 534, a first lens 536, and a second lens 538, similar in structure and function to the light source 311, pattern screen 334, first lens 336, and second lens 338 described above with respect to FIGS. 10A and 10B. The imaging subsystem comprises a lens 552, an optical fiber bundle 554, and a camera (not shown) located at the proximal end of the instrument, similar in structure and function to the lens 252, optical fiber bundle 254, and camera described above with respect to FIGS. 9A and 9B.

FIG. 13A shows another example of a distal end of an instrument, showing the distal tip of a probe 680 in a partial cut-away view. FIG. 13B shows a top view of the distal tip of the probe 680. The instrument has illumination and imaging subsystems that are similar in structure and function to that described above with respect to FIGS. 11A and 11B. The illumination subsystem comprises a light source (not shown) at the proximal end of the instrument, an optical fiber 632, a pattern screen 634, a first lens 636, and a second lens 638, similar in structure and function to the light source, optical fiber 232, pattern screen 234, first lens 236, and second lens 238 described above with respect to FIGS. 9A and 9B. The imaging subsystem comprises a lens 652 and a camera 656 at the distal end of the instrument, similar in structure and function to the lens 352 and camera 356 described above with respect to FIGS. 10A and 10B. In the examples of FIGS. 9A-9B, 10A-10B, 11A-11B, and 12A-12B, the direction of the projection of the pattern and the direction of the image capture are aligned with the longitudinal axis of the probe. The imaging optics face forward, making the probe "forward-looking". In the example of FIGS. 13A-13B, the distal tip of the probe is designed so that the projection of the pattern and the capturing of the images is done at an angle to the axis of the probe. The imaging optics face to the side, making the probe "side-looking". The distal tip of the tube of the probe has a surface 628 that is angled with respect to the axis of the probe, for example forming an angle of 30 degrees (or in the range of 10 degrees to 90 degrees) with the axis of the probe. The optical fiber(s) 632 has a bend near the distal end to direct the illumination optics including lens 238 normal to the angled surface 628 of the probe, so that an optical axis of the illumination optics is normal to the angled surface 628 of the probe. Similarly, the wiring for the camera 656 bends so that the camera 656 and lens 652 are directed normal to the angled surface 628 of the probe, so that an optical axis of the imaging optics is normal to the angled surface 628 of the probe. An orientation that directs the projection of the pattern and the capturing of the images at an angle with respect to the axis of the probe can help obtain images around the full ear canal. The user can maneuver the probe by turning it to face the projection optics and camera at different target surfaces around the ear canal.

Figure 14:
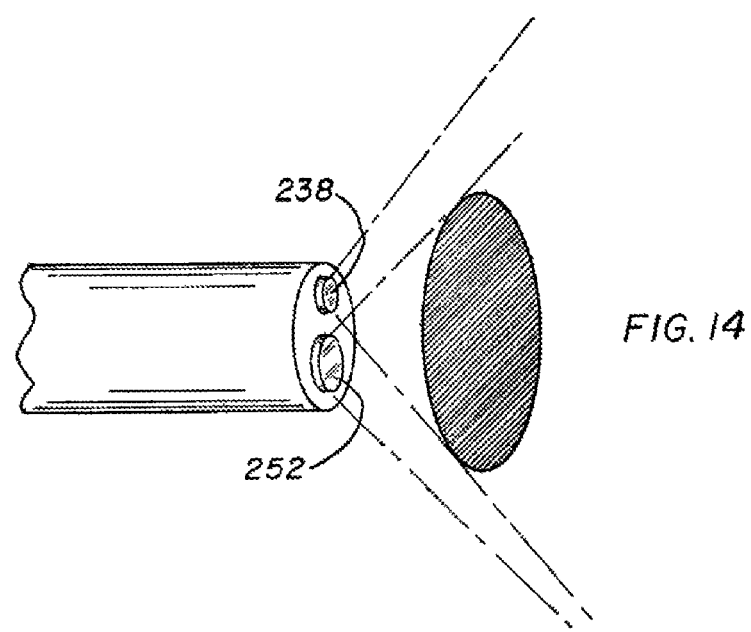
FIG. 14 schematically illustrates an area of overlap of a projected pattern and an area of image capture.

FIG. 14 schematically illustrates an area of overlap of a projected pattern and an area of image capture. The lens 238 of the projection optics may be a wide-angle lens to project the pattern over a wide area. Similarly, the lens 252 of the imaging optics may be a wide-angle lens that enables the camera to capture an image over a wide area. The area of overlap between the projected pattern and the captured image is shown. As stated above, the lens 252 may be a wide-angle lens that enables the camera to capture in one image a full cross-section or up to 180-degree view of the ear canal. Alternatively, it may capture a smaller area in one image, and the probe can be maneuvered as needed to image the entire desired ear canal area.

Figure 15:
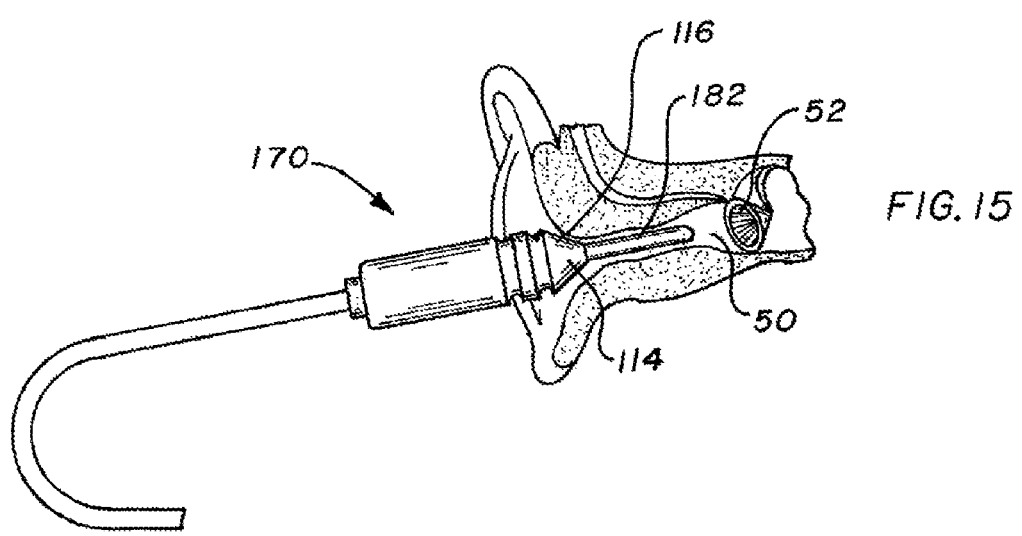
FIG. 15 shows use of the instrument of FIG. 8.

FIG. 15 shows use of an instrument comprising probe 180. The user holds the probe and maneuvers the distal tube 182 into the ear canal 50. The imaging subsystem is turned on, and with each frame the camera captures an image of the pattern projected onto the ear canal surface (including, if desired, the surface of the eardrum 52). The user maneuvers the tube 182 distally into the ear canal 50, and/or around the ear canal 50, while the camera captures successive images. The wide portion of the probe, and in particular the wider end 116 of the tapered stop 114, prevents the user from pushing the tube 182 too far into the ear canal 50, thereby protecting the eardrum 52.

Figure 16:
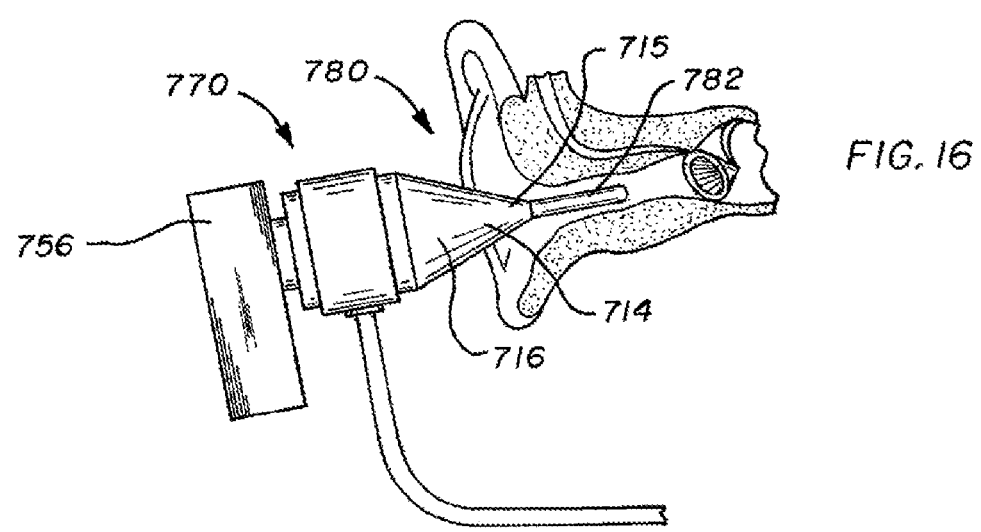
FIG. 16 shows an alternate instrument that is a component of a system for generating a three-dimensional model of an ear canal.

FIG. 16 shows an alternate instrument 770 that is a component of a system for generating a three-dimensional model of the ear canal. The instrument 770 comprises a probe 780 at its distal end. The probe 780 has a narrow portion in the form of a rigid or semi-rigid tube 782 at its distal end. The probe 780 include a tapered stop 714 that is narrower at one end 715 than the other end 716. The tube 782 is connected to the narrower end 715 of the tapered stop 714. The wider end 716 of the tapered stop 714 forms the wide portion of the probe 780. The tapered stop 714 is oriented so that its narrower end 715 faces the tube 782 and thus faces toward the ear. The narrow portion or tube 782 can fit inside the ear canal, while the wide portion or wider end 716 of the tapered stop 714 cannot fit inside the ear canal. Thus, the wide portion of the probe, and in particular the wider end 716 of the tapered stop 714, acts as a stop that prevents the narrow portion of the probe from being inserted too far into the ear canal, so as to prevent damage to the eardrum or other injury.

The instrument 770 carries a camera 756 that is part of the imaging subsystem. The imaging subsystem is similar to the imaging subsystem in FIGS. 9A-9B in that the camera is not located in the probe but rather is kept external to the ear, with a coherent fiber optic bundle connecting the camera to a lens at the distal end of the probe.

Figure 17:
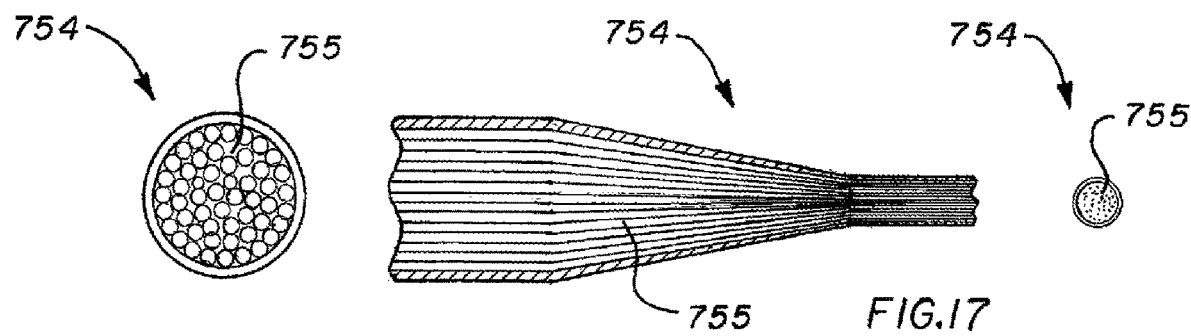
FIG. 17 shows an example of a fiber optic bundle that is usable with the instrument of FIG. 16.

FIG. 17 shows an example of a fiber optic bundle 754 that is usable with the instrument 770. The fiber optic bundle 754 comprises a plurality of individual optical fibers 755 arranged in a manner that preserves their relative orientation from the distal end of the probe to the camera. The fiber optic bundle 754 may be tapered such that a small profile at the distal end of the probe can be expanded to a larger viewing area for the camera 756. The camera 756 may have a display screen that displays in real time the surface of the ear canal. In this manner, the user (e.g., physician) can use the instrument as an otoscope for inspection of the ear in addition to using it to generate the three-dimensional model. Similarly, in other embodiments, a display may be used, e.g., a display on the camera itself and/or an associated computer display or other display, in order to show in real time the view at the distal tip of the probe, for use of the instrument as an otoscope as well as for guidance in selecting areas for scanning and modeling.

Figure 18:
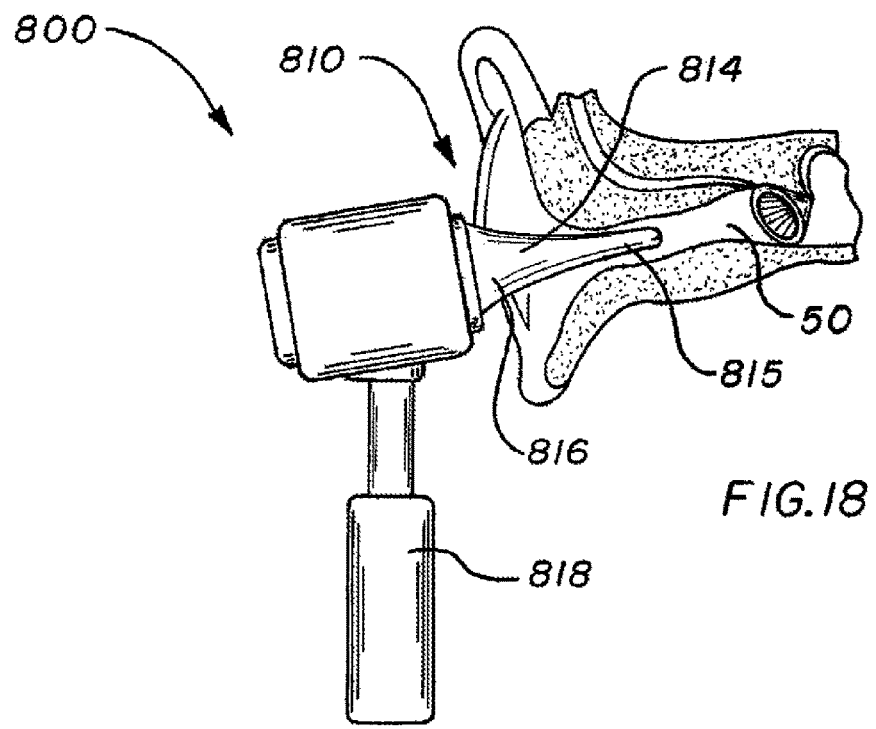
FIG. 18 shows another alternate instrument that is a component of a system for generating a three-dimensional model of an ear canal.

FIG. 18 shows another alternate instrument 800 that is a component of a system for generating a three-dimensional model of the ear canal. The instrument 800 comprises a probe 810 at its distal end. The probe 810 include a tapered stop 814 that is narrower at one end 815 than the other end 816. The narrower end 815 of the tapered stop 814 forms the narrow portion of the probe 810. The wider end 816 of the tapered stop 814 forms the wide portion of the probe 810. The tapered stop 814 is oriented so that its narrower end 815 faces toward the ear. The narrow portion or narrower end 815 of the tapered stop 814 can fit inside the ear canal 50, while the wide portion or wider end 816 of the tapered stop 814 cannot fit inside the ear canal. Thus, the wide portion of the probe, and in particular the wider end 816 of the tapered stop 814, acts as a stop that prevents the narrow portion of the probe from being inserted too far into the ear canal, so as to prevent damage to the eardrum or other injury. The instrument 800 has a handle 818 connected to the wider end 816 of the tapered stop. The handle 818 allows the user to maneuver the probe 810 within the ear canal to obtain the desired views (similar, for example, to handle 118).

In addition to the instruments and probes described above, and the illumination and imaging subsystems described above, a system for generating a three-dimensional model of an ear canal may further comprise a computer subsystem with one or more processors, memory, and software. The software comprises a spatial signal modulation algorithm for converting each individual image in the series of successive images from the video camera into an individual digital point cloud, each individual digital point cloud representing a three-dimensional model of a part the ear canal surface. The computer subsystem calculates an individual digital point cloud for each individual image.

In SSM, a 2-dimensional (2-d) signal with its intensity level varying across a distance (as opposed to varying over time as in radio signals), is generated by the pattern screen and projected through the lens(es) onto a 3-dimensional (3-d) target to be modeled. The 3-d shape of the target surface modulates, or changes, the signal which is then reflected back and imaged by the camera. Given prior knowledge of the original transmitted signal, the changes to the imaged reflection can be isolated and the continuous quantitative 3-d shape of the target surface can be calculated. There are many types of algorithms that may be employed to analyze the modulated spatial signals, including: moire interferometry, fringe projection, Fourier transform or deconvolution profilometry, and others. Image corrections may be used to account for aberrations caused by the optical system, including radial aberrations (commonly barrel or pincushion distortions), misalignment, or lens edge distortions. These can be corrected for during a one-time systemic calibration procedure which identifies and quantifies the unique optical effects in the system and determines the mathematical corrections to negate their influence. These aberration definitions can then be quickly applied to produce properly compensated images to be used for SSM 3-d modeling.

The computer subsystem can calculate an individual digital point cloud for each individual image from the camera at or faster than the frame rate of the camera. In this way, the display can show a display of the calculated three-dimensional surface being imaged in real time (e.g., at 25 frames per second, 30 frames per second, or faster, such as thousands of frames per second).

The software may further comprise a stitching algorithm for stitching together the individual digital point clouds into an overall digital point cloud, the overall digital point cloud representing a three-dimensional model of the ear canal. For example, each point cloud in a succession of frames changes from the previous point cloud due to the incremental movement occurring relative to the previous frame. The bulk of the point cloud data is identical to the one preceding it, but it includes the addition of a small portion that was not present in the previous frame due to a change in relative position during the small interframe time interval. Mathematical processing identifies these areas that have changed and adds, or stitches them, onto the overall 3-d model. Each successive frame causes another incremental addition to the model, eventually resulting in a single large continuous 3-d surface model of the entire volume under study. Each frame of surface data can be thought of as overlapping pieces of a mosaic representing the chamber into which the probe was inserted. The addition of data to each frame from an inertial navigation device would be beneficial by explicitly locating that frame in space, thereby assisting with model reconstruction or permitting closer inspection of details contained within that individual point cloud.

The following describes a method of using a system as described above to generate a three-dimensional model of an ear canal, and optionally to also manufacture an earmold, such as for a hearing aid, based upon that three-dimensional model of an ear canal. First, the user (e.g., physician) handles the instrument and maneuvers the distal tip of the probe into the ear canal. The illumination subsystem is activated, causing the light source to project light through the pattern screen, the patterned light passing through the lens(es) and being projected onto the target surface of the ear canal. The imaging subsystem is activated, and the camera continuously captures a series of successive individual images of the pattern as projected on and modulated by the target surface. The camera captures an individual image for each frame of video. The individual images in the series of successive individual images differ from each other due to relative movement between the probe and the surface being imaged. As the probe is moved, different images are captured. The user maneuvers the probe to obtain images of the entire surface that is desired to be modeled, including all or part of the ear canal and, if desired, the ear drum and/or all or part of the outer ear. The computer system and software comprising the spatial signal modulation algorithm uses each individual image in the series of images as input and, at or faster than frame rates, creates an individual digital point cloud, or three-dimensional map, for each individual image in the series of successive images. Each individual digital point cloud may be generated from the entire corresponding image or, if desired in order to eliminate edge distortion, from only a central portion of the corresponding image. For example, the central 70% to 80% of the image field may be used in order to minimize the effects of optical distortion near the lens boundaries. Each individual digital point cloud represents a three-dimensional model of a part the ear canal surface. By generating the digital point clouds at the frame rate of the camera, the systems enables a display to show in real time, at frame rates of the camera, a live and nearly instantaneous three-dimensional, full-field representation of the surface being viewed. The computer system and software comprising the stitching algorithm registers and stitches together the individual digital point clouds into an overall digital point cloud, the overall digital point cloud representing a three-dimensional model or map of the ear canal. Thus, the system performs continuous mapping at rapid frame rates, and it assembles the individual surface models into single continuous entity.

Using the three-dimensional model of the ear canal, a system for manufacturing an earmold may use a three-dimensional printer to print the earmold, or to print a mold in which the earmold is subsequently molded, or to print a part in the shape of the desired earmold, from which the earmold is then made by molding or thermoforming. In another alternative, a system for manufacturing an earmold using the three-dimensional model of the ear canal machines or otherwise manufactures a mold based upon the three-dimensional model of the ear canal and then molds the earmold using that mold.

A system as described herein to generate a three-dimensional model of an ear canal, and optionally to also manufacture an earmold, has a number of advantages. The device generates highly accurate three-dimensional models, facilitating the manufacture of well-fitting earmolds. The device takes measurements quickly, thereby reducing the time needed from the user (physician) and patient. The device has a small and maneuverable profile, enabling measurements through the narrow and tortuous ear canal and deep into the ear canal, including measurements of the eardrum. The device's rapid measurements make it less susceptible to irregularities due to anatomical movement, which can be present in the ear canal because the pliable or semi-rigid tissue can change shape with patient movement, respiration, muscle contractions, jaw positions, etc. The device can quickly and easily make multiple models, such as of the same ear canal with the patient's jaw in different positions. The device does not have the discomfort of inserting an impression material into an ear and leaving it in place during curing. The device is reliable, with no moving parts, lessening potential for damage or breaking. The device may be used as an otoscope for ear inspection as well as for three-dimensional scanning and model generation. The device is easy to clean. The distal part of the probe may be provided with a disposable cover that can be discarded and replaced after each patient.

As persons having ordinary skill in the art would understand from the above descriptions and accompanying drawings, various systems and methods are disclosed herein for providing three-dimensional representations of a target surface of a human body. In some embodiments, the system comprises an instrument comprising a probe (e.g., the catheters shown in FIGS. 4A, 4B, 4C, 5, 7A, and 7B may be considered probes, as well as the probes in FIGS. 8-18), the probe having a distal end sized to fit within a lumen (e.g., a gastrointestinal tract, a blood vessel, an ear canal, etc.) of the human body and adapted to be directed through the lumen to the target surface of the human body. In example embodiments, the system further comprises projection components for projecting electromagnetic radiation onto the target surface in a projected pattern, the projection components comprising an electromagnetic radiation emitter, a pattern screen (e.g., a slide or grating with a desired pattern, such as pattern screens 502, 234, 334, 434, 534, and 634), and a projection lens, with at least the projection lens being located at the distal end of the probe. In such embodiments, the projection components are configured to project electromagnetic radiation from the electromagnetic radiation emitter, through the pattern screen, and through the projection lens in order to project a pattern of electromagnetic radiation (e.g., ultraviolet light, visible light, infrared light) from the distal end of the probe onto the target surface. In example embodiments, the system further comprises imaging components for capturing a plurality of successive images of electromagnetic radiation reflected from the target surface, the imaging components comprising an imaging lens and an image sensor configured to capture image data, with at least the imaging lens being located at the distal end of the probe, wherein the imaging components are configured such that each frame of the image sensor captures an image comprising a reflection of the projected pattern modulated by the target surface, and wherein with multiple successive frames of the image sensor, the image sensor is configured to capture a plurality of successive images that differ from each other due to relative movement between the probe and the target surface. In example embodiments, the system further comprises an image processing module configured to receive the captured image data from the image sensor and to calculate a three-dimensional representation of the target surface for each image of the plurality of successive images using the captured image data and a spatial signal modulation algorithm, resulting in a plurality of successive three-dimensional representations of the target surface. The image processing module may be adapted to stitch together the plurality of successive three-dimensional representations of the target surface. The system may further be adapted to display the plurality of successive three-dimensional representations of the target surface on a display device.

The embodiments described and illustrated herein are only examples, as many variations are possible. The materials, dimensions, components, order of steps, and operation may be varied without departing from the scope of the invention, which is limited only by the appended claims. Those skilled in the art may appreciate from the foregoing description that the present invention may be implemented in a variety of forms, and that the various embodiments may be implemented alone or in combination. Therefore, while the embodiments of the present invention have been described in connection with particular examples thereof, the true scope of the embodiments and/or methods of the present invention should not be so limited since other modifications will become apparent to the skilled practitioner upon a study of the drawings, specification, and following claims.

What is claimed is:

1. A system for providing a three-dimensional representation of a target surface of a human body, the system comprising:
   an instrument comprising a probe, the probe having a distal end sized to fit within a lumen of the human body and adapted to be directed through the lumen to the target surface of the human body;
   projection components for projecting electromagnetic radiation onto the target surface in a projected pattern, the projection components comprising an electromagnetic radiation emitter, a pattern screen, and a projection lens, with at least the projection lens being located at the distal end of the probe, wherein the projection components are configured to project electromagnetic radiation from the electromagnetic radiation emitter, through the pattern screen, and through the projection lens in order to project a pattern of electromagnetic radiation from the distal end of the probe onto the target surface;
   imaging components for capturing a plurality of successive images of electromagnetic radiation reflected from the target surface, the imaging components comprising an imaging lens and an image sensor configured to capture image data, with at least the imaging lens being located at the distal end of the probe, wherein the imaging components are configured such that each frame of the image sensor captures an image comprising a reflection of the projected pattern modulated by the target surface, and wherein with multiple successive frames of the image sensor, the image sensor is configured to capture a plurality of successive images that differ from each other due to relative movement between the probe and the target surface; and
   an image processing module configured to receive the captured image data from the image sensor and to calculate a three-dimensional representation of the target surface for each image of the plurality of successive images using the captured image data and a spatial signal modulation algorithm, resulting in a plurality of successive three-dimensional representations of the target surface.

2. A system as recited in claim 1, wherein the image processing module is adapted to stitch together the plurality of successive three-dimensional representations of the target surface.

3. A system as recited in claim 1, wherein the image sensor is located at the distal end of the probe.

4. A system as recited in claim 1, wherein the image sensor is located at a proximal end of the probe.

5. A method for providing a three-dimensional representation of a target surface of a human body, the method comprising:
directing a distal end of a probe within a lumen of the human body to the target surface of the human body;
projecting electromagnetic radiation onto the target surface in a projected pattern using projection components, the projection components comprising an electromagnetic radiation emitter, a pattern screen, and a projection lens, with at least the projection lens being located at the distal end of the probe, wherein electromagnetic radiation that is emitted from the electromagnetic radiation emitter and that passes through the pattern screen and the projection lens is projected onto the target surface;
capturing image data by an image sensor, wherein each frame of the image sensor captures an image comprising a reflection of the projected pattern modulated by the target surface, and wherein with multiple successive frames of the image sensor, the image sensor captures a plurality of successive images that differ from each other due to relative movement between the probe and the target surface;
providing the captured image data to an image processing module;
calculating, by the image processing module, a three-dimensional representation of the target surface for each image of the plurality of successive images using the captured image data and a spatial signal modulation algorithm, resulting in a plurality of successive three-dimensional representations of the target surface.

6. A method as recited in claim 5, further comprising displaying the plurality of successive three-dimensional representations of the target surface on a display device.

7. A method as recited in claim 5, further comprising stitching together the plurality of successive three-dimensional representations of the target surface.

8. A method as recited in claim 5, wherein the image sensor is located at the distal end of the probe.

9. A method as recited in claim 5, wherein the image sensor is located at a proximal end of the probe.

10. A method as recited in claim 5, wherein the pattern screen is a fixed component, and the pattern of the pattern screen is constant and does not change.

11. A system as recited in claim 1, wherein the pattern screen is a fixed component, and the pattern of the pattern screen is constant and does not change.

12. A system for providing a three-dimensional representation of a target surface of a human body, the system comprising:
an instrument comprising a probe, the probe having a distal end sized to fit within a lumen of the human body and adapted to be directed through the lumen to the target surface of the human body;
projection components for projecting electromagnetic radiation onto the target surface in a projected pattern, the projection components comprising an electromagnetic radiation emitter, a pattern slide or grating, and a projection lens, with at least the projection lens being located at the distal end of the probe, wherein the projection components are configured to project electromagnetic radiation from the electromagnetic radiation emitter, through the pattern slide or grating, and through the projection lens in order to project a pattern of electromagnetic radiation from the distal end of the probe onto the target surface;
imaging components for capturing a plurality of successive images of electromagnetic radiation reflected from the target surface, the imaging components comprising an imaging lens and an image sensor configured to capture image data, with at least the imaging lens being located at the distal end of the probe, wherein the imaging components are configured such that each frame of the image sensor captures an image comprising a reflection of the projected pattern modulated by the target surface, and wherein with multiple successive frames of the image sensor, the image sensor is configured to capture a plurality of successive images that differ from each other due to relative movement between the probe and the target surface; and
an image processing module configured to receive the captured image data from the image sensor and to calculate a three-dimensional representation of the target surface for each image of the plurality of successive images using the captured image data and a spatial signal modulation algorithm, resulting in a plurality of successive three-dimensional representations of the target surface;
wherein the image processing module is adapted to stitch together the plurality of successive three-dimensional representations of the target surface; and
wherein the pattern slide or grating is a fixed component, and the pattern of the pattern slide or grating is constant and does not change.

13. A system as recited in claim 12, wherein the image sensor is located at the distal end of the probe.

14. A system as recited in claim 12, wherein the image sensor is located at a proximal end of the probe.

15. A method for providing a three-dimensional representation of a target surface of a human body, the method comprising:
directing a distal end of a probe within a lumen of the human body to the target surface of the human body;
projecting electromagnetic radiation onto the target surface in a projected pattern using projection components, the projection components comprising an electromagnetic radiation emitter, a pattern slide or grating, and a projection lens, with at least the projection lens being located at the distal end of the probe, wherein electromagnetic radiation that is emitted from the electromagnetic radiation emitter and that passes through the pattern slide or grating and the projection lens is projected onto the target surface;
capturing image data by an image sensor, wherein each frame of the image sensor captures an image comprising a reflection of the projected pattern modulated by the target surface, and wherein with multiple successive frames of the image sensor, the image sensor captures a plurality of successive images that differ from each other due to relative movement between the probe and the target surface;
providing the captured image data to an image processing module;
calculating, by the image processing module, a three-dimensional representation of the target surface for each image of the plurality of successive images using the captured image data and a spatial signal modulation algorithm, resulting in a plurality of successive three-dimensional representations of the target surface; and displaying the plurality of successive three-dimensional representations of the target surface on a display device;

wherein the pattern slide or grating is a fixed component, and the pattern of the pattern slide or grating is constant and does not change.

16. A method as recited in claim 15, further comprising stitching together the plurality of successive three-dimensional representations of the target surface.

17. A method as recited in claim 15, wherein the image sensor is located at the distal end of the probe.

18. A method as recited in claim 15, wherein the image sensor is located at a proximal end of the probe.

\* \* \* \* \*